(12) United States Patent
Liu et al.

(10) Patent No.: US 8,420,868 B2
(45) Date of Patent: *Apr. 16, 2013

(54) PROCESS FOR THE PREPARATION OF 2,2,4,4-TETRAALKYLCYCLOBUTANE-1,3-DIOLS

(75) Inventors: Zhufang Liu, Kingsport, TN (US); Lori Cooke Ensor, Blountville, TN (US); Guy Ralph Steinmetz, Kingsport, TN (US); Jerome Leonard Stavinoha, Jr., Longview, TX (US)

(73) Assignee: Eastman Chemical Company, Kingsport, TN (US)

( * ) Notice: Subject to any disclaimer, the term of this patent is extended or adjusted under 35 U.S.C. 154(b) by 203 days.

This patent is subject to a terminal disclaimer.

(21) Appl. No.: 12/963,691

(22) Filed: Dec. 9, 2010

(65) Prior Publication Data

US 2012/0149946 A1  Jun. 14, 2012

(51) Int. Cl.
*C07C 29/145* (2006.01)
*C07C 35/04* (2006.01)

(52) U.S. Cl.
USPC ............................................ 568/839

(58) Field of Classification Search .............. 568/839
See application file for complete search history.

(56) References Cited

U.S. PATENT DOCUMENTS

| | | | |
|---|---|---|---|
| 1,602,699 A | 10/1926 | Nightingale |
| 2,160,841 A | 6/1939 | Dreyfus |
| 2,202,046 A | 5/1940 | Dreyfus et al. |
| 2,278,537 A | 4/1942 | Dreyfus et al. |
| 2,720,507 A | 10/1955 | Caldwell |
| 2,806,064 A | 9/1957 | McKlveen |
| 2,901,466 A | 8/1959 | Kibler |
| 2,936,324 A | 5/1960 | Hasek et al. |
| 3,000,906 A | 9/1961 | Hasek et al. |
| 3,030,335 A | 4/1962 | Goldberg |
| 3,062,852 A | 11/1962 | Martin et al. |
| 3,075,952 A | 1/1963 | Coover et al. |
| 3,091,600 A | 5/1963 | Caldwell et al. |
| 3,169,121 A | 2/1965 | Goldberg et al. |
| 3,190,928 A | 6/1965 | Elam et al. |
| 3,201,474 A | 8/1965 | Hasek et al. |
| 3,207,814 A | 9/1965 | Goldberg et al. |
| 3,218,372 A | 11/1965 | Okamura et al. |
| 3,227,764 A | 1/1966 | Martin et al. |
| 3,236,899 A | 2/1966 | Clark |
| 3,249,652 A | 5/1966 | Quisenberry |
| 3,259,469 A | 7/1966 | Painter et al. |
| 3,287,390 A | 11/1966 | Poos et al. |
| 3,288,854 A | 11/1966 | Martin |
| 3,312,741 A | 4/1967 | Martin |
| 3,313,777 A | 4/1967 | Elam et al. |
| 3,317,466 A | 5/1967 | Caldwell et al. |
| 3,329,722 A | 7/1967 | Rylander |
| 3,360,547 A | 12/1967 | Wilson et al. |
| 3,366,689 A | 1/1968 | Maeda et al. |
| 3,386,935 A | 6/1968 | Jackson et al. |
| 3,403,181 A | 9/1968 | Painter et al. |
| T858012 I4 | 1/1969 | Caldwell et al. |
| 3,484,339 A | 12/1969 | Caldwell |
| 3,502,620 A | 3/1970 | Caldwell |
| T873016 I4 | 4/1970 | Gilkey et al. |
| 3,541,059 A | 11/1970 | Schaper |
| 3,546,177 A | 12/1970 | Kibler et al. |
| 3,629,202 A | 12/1971 | Gilkey et al. |
| RE27,682 E | 6/1973 | Schnell et al. |
| 3,772,405 A | 11/1973 | Hamb |
| 3,799,953 A | 3/1974 | Freitag et al. |
| 3,907,754 A | 9/1975 | Tershansy et al. |
| 3,915,913 A | 10/1975 | Jackson, Jr. et al. |
| 3,962,189 A | 6/1976 | Russin et al. |
| 4,001,184 A | 1/1977 | Scott |
| 4,010,145 A | 3/1977 | Russin et al. |
| 4,046,933 A | 9/1977 | Stefanik |
| 4,056,504 A | 11/1977 | Grundmeier et al. |
| 4,084,889 A | 4/1978 | Vischer, Jr. |
| 4,125,572 A | 11/1978 | Scott |
| 4,156,069 A | 5/1979 | Prevorsek et al. |
| 4,160,383 A | 7/1979 | Rauschenberger |
| 4,185,009 A | 1/1980 | Idel et al. |
| 4,188,314 A | 2/1980 | Fox et al. |
| 4,194,038 A | 3/1980 | Baker et al. |
| 4,263,364 A | 4/1981 | Seymour et al. |

(Continued)

FOREIGN PATENT DOCUMENTS

| | | |
|---|---|---|
| BE | 615850 | 4/1962 |
| CA | 2035149 | 8/1991 |

(Continued)

OTHER PUBLICATIONS

Abstract of U.S. Defense Publication T869,015, 869 O.G. 714, Dec. 16, 1969.

Abstract of U.S. Defense Publication T875,010, 875 O.G. 342, Jun. 9, 1970.

Chen et al., "The molecular basis for the relationship between the secondary relaxation and mechanical properties of a series of polyester copolymer glasses," Marcromolecules, 32:5944-5955 (1999).

Kelsey, E. et al., "High Impact, Amorphous Terephthalate Copolyesters of Rigid 2,2,4,4-Tetramethyl-1,3-cyclobutanediol with Flexible Diols," Macromolecules, vol. 33, 2000, pp. 5810-5818, American Chemical Society.

(Continued)

*Primary Examiner* — Brian J Davis
(74) *Attorney, Agent, or Firm* — Jennifer R. Knight; Eric D. Middlemas

(57) ABSTRACT

Disclosed is a process for the preparation of a 2,2,4,4-tetraalkylcyclobutane-1,3-diols by hydrogenation of a 2,2,4,4-tetraalkylcyclobutane-1,3-dione in the presence of a catalyst comprising ruthenium deposited on a carbon nanotube support. The process is useful for the preparation of 2,2,4,4-tetramethylcyclobutane-1,3-diol. The process may be carried out in the presence or absence of a solvent and in the liquid or vapor phase. Also disclosed is a process for modifying the cis:trans ratio of the 2,2,4,4-tetramethylcyclobutane-1,3-diol hydrogenation product by contacting the diol with hydrogen in the presence of a supported ruthenium catalyst.

16 Claims, 1 Drawing Sheet

U.S. PATENT DOCUMENTS

| | | | |
|---|---|---|---|
| 4,356,299 A | 10/1982 | Cholod et al. |
| 4,367,186 A | 1/1983 | Adelmann et al. |
| 4,379,802 A | 4/1983 | Weaver et al. |
| 4,384,106 A | 5/1983 | Go et al. |
| 4,391,954 A | 7/1983 | Scott |
| 4,424,140 A | 1/1984 | Weinberg et al. |
| 4,426,512 A | 1/1984 | Barbee et al. |
| 4,427,614 A | 1/1984 | Barham et al. |
| 4,430,484 A | 2/1984 | Quinn |
| 4,431,793 A | 2/1984 | Rosenquist |
| 4,452,933 A | 6/1984 | McCready |
| 4,465,820 A | 8/1984 | Miller et al. |
| 4,469,861 A | 9/1984 | Mark et al. |
| 4,480,086 A | 10/1984 | O'Neill |
| 4,525,504 A | 6/1985 | Morris et al. |
| 4,578,295 A | 3/1986 | Jabarin |
| 4,578,437 A | 3/1986 | Light et al. |
| 4,642,959 A | 2/1987 | Swiech, Jr. et al. |
| 4,738,880 A | 4/1988 | Asada et al. |
| 4,749,773 A | 6/1988 | Weaver et al. |
| 4,786,692 A | 11/1988 | Allen et al. |
| 4,816,308 A | 3/1989 | Shimizu et al. |
| 4,826,903 A | 5/1989 | Weaver et al. |
| 4,845,188 A | 7/1989 | Weaver et al. |
| 4,880,592 A | 11/1989 | Martini et al. |
| 4,882,412 A | 11/1989 | Weaver et al. |
| 4,892,922 A | 1/1990 | Weaver et al. |
| 4,892,923 A | 1/1990 | Weaver et al. |
| 4,937,134 A | 6/1990 | Schrenk et al. |
| 4,939,186 A | 7/1990 | Nelson et al. |
| 4,976,057 A | 12/1990 | Bianchi |
| 4,981,898 A | 1/1991 | Bassett |
| 4,985,342 A | 1/1991 | Muramoto et al. |
| 5,017,679 A | 5/1991 | Chang et al. |
| 5,017,680 A | 5/1991 | Sublett |
| 5,034,252 A | 7/1991 | Nilsson et al. |
| 5,104,450 A | 4/1992 | Sand et al. |
| 5,118,760 A | 6/1992 | Blakely et al. |
| 5,118,847 A | 6/1992 | Jackson et al. |
| 5,142,088 A | 8/1992 | Phelps et al. |
| 5,169,994 A | 12/1992 | Sumner, Jr. et al. |
| 5,183,863 A | 2/1993 | Nakamura et al. |
| 5,191,038 A | 3/1993 | Krabbenhoft et al. |
| 5,207,967 A | 5/1993 | Small, Jr. et al. |
| 5,219,510 A | 6/1993 | Machell et al. |
| 5,224,958 A | 7/1993 | Warunek et al. |
| 5,239,020 A | 8/1993 | Morris |
| 5,256,761 A | 10/1993 | Blount, Jr. |
| 5,258,556 A | 11/1993 | Sumner, Jr. et al. |
| 5,268,219 A | 12/1993 | Harada et al. |
| 5,288,715 A | 2/1994 | Machell et al. |
| 5,288,764 A | 2/1994 | Rotter et al. |
| 5,292,783 A | 3/1994 | Buchanan et al. |
| 5,310,611 A | 5/1994 | Okabe et al. |
| 5,310,787 A | 5/1994 | Kutsuwa et al. |
| 5,326,584 A | 7/1994 | Kamel et al. |
| 5,326,821 A | 7/1994 | Sasaki et al. |
| 5,331,034 A | 7/1994 | Pfahler et al. |
| 5,333,073 A | 7/1994 | Suzuki |
| 5,354,791 A | 10/1994 | Gallucci |
| 5,372,864 A | 12/1994 | Weaver et al. |
| 5,372,879 A | 12/1994 | Handa et al. |
| 5,378,796 A | 1/1995 | George et al. |
| 5,382,292 A | 1/1995 | Conroy et al. |
| 5,384,377 A | 1/1995 | Weaver et al. |
| 5,475,144 A | 12/1995 | Watson et al. |
| 5,480,926 A | 1/1996 | Fagerburg et al. |
| 5,486,562 A | 1/1996 | Borman et al. |
| 5,489,665 A | 2/1996 | Yamato et al. |
| 5,494,992 A | 2/1996 | Kanno et al. |
| 5,498,668 A | 3/1996 | Scott |
| 5,498,688 A | 3/1996 | Oshino et al. |
| 5,506,014 A | 4/1996 | Minnick |
| 5,523,382 A | 6/1996 | Beavers et al. |
| 5,534,609 A | 7/1996 | Lewis et al. |
| 5,552,512 A | 9/1996 | Sublett |
| 5,591,530 A | 1/1997 | Warner et al. |
| 5,633,340 A | 5/1997 | Hoffman et al. |
| 5,650,453 A | 7/1997 | Eckberg et al. |
| 5,654,347 A | 8/1997 | Khemani et al. |
| 5,656,715 A | 8/1997 | Dickerson et al. |
| 5,668,243 A | 9/1997 | Yau et al. |
| 5,681,918 A | 10/1997 | Adams et al. |
| 5,688,874 A | 11/1997 | Hoffman |
| 5,696,176 A | 12/1997 | Khemani et al. |
| 5,705,575 A | 1/1998 | Kelsey |
| 5,783,307 A | 7/1998 | Fagerburg et al. |
| 5,804,617 A | 9/1998 | Hoffman et al. |
| 5,814,679 A | 9/1998 | Eckberg et al. |
| 5,859,116 A | 1/1999 | Shih |
| 5,863,622 A | 1/1999 | Jester |
| 5,902,631 A | 5/1999 | Wang et al. |
| 5,907,026 A | 5/1999 | Factor et al. |
| 5,942,585 A | 8/1999 | Scott et al. |
| 5,955,565 A | 9/1999 | Morris et al. |
| 5,958,539 A | 9/1999 | Eckart et al. |
| 5,958,581 A | 9/1999 | Khanarian et al. |
| 5,959,066 A | 9/1999 | Charbonneau et al. |
| 5,962,625 A | 10/1999 | Yau |
| 5,977,347 A | 11/1999 | Shuto et al. |
| 5,989,663 A | 11/1999 | Morris et al. |
| 6,001,910 A | 12/1999 | Blumenthal et al. |
| 6,005,059 A | 12/1999 | Scott et al. |
| 6,011,124 A | 1/2000 | Scott et al. |
| 6,012,597 A | 1/2000 | Nishihara et al. |
| 6,022,603 A | 2/2000 | Umeda et al. |
| 6,025,061 A | 2/2000 | Khanarian et al. |
| 6,030,671 A | 2/2000 | Yang et al. |
| 6,037,424 A | 3/2000 | Scott et al. |
| 6,043,322 A | 3/2000 | Scott et al. |
| 6,044,996 A | 4/2000 | Carew et al. |
| 6,063,464 A | 5/2000 | Charbonneau et al. |
| 6,063,465 A | 5/2000 | Charbonneau et al. |
| 6,063,495 A | 5/2000 | Charbonneau et al. |
| 6,084,019 A | 7/2000 | Matayabas et al. |
| 6,096,854 A | 8/2000 | Morris et al. |
| 6,114,575 A | 9/2000 | McMahon et al. |
| 6,120,477 A | 9/2000 | Campbell et al. |
| 6,120,889 A | 9/2000 | Turner et al. |
| 6,126,992 A | 10/2000 | Khanarian et al. |
| 6,127,492 A | 10/2000 | Nagashima et al. |
| 6,146,228 A | 11/2000 | Mougin et al. |
| 6,150,494 A | 11/2000 | Wang et al. |
| 6,183,848 B1 | 2/2001 | Turner et al. |
| 6,191,209 B1 | 2/2001 | Andrews et al. |
| 6,211,309 B1 | 4/2001 | McIntosh et al. |
| 6,221,556 B1 | 4/2001 | Gallucci et al. |
| 6,225,436 B1 | 5/2001 | Eiffler et al. |
| 6,232,504 B1 | 5/2001 | Barteau et al. |
| 6,239,210 B1 | 5/2001 | Kim et al. |
| 6,255,523 B1 | 7/2001 | Panandiker et al. |
| 6,287,656 B1 | 9/2001 | Turner et al. |
| 6,307,006 B1 | 10/2001 | Konig et al. |
| 6,309,718 B1 | 10/2001 | Sprayberry |
| 6,320,042 B1 | 11/2001 | Michihata et al. |
| 6,323,291 B1 | 11/2001 | Mason et al. |
| 6,323,304 B1 | 11/2001 | Lemmon et al. |
| 6,342,304 B1 | 1/2002 | Buchanan et al. |
| 6,352,783 B1 | 3/2002 | Fagerburg |
| 6,354,986 B1 | 3/2002 | Hlavinka et al. |
| 6,359,070 B1 | 3/2002 | Khanarian et al. |
| 6,406,792 B1 | 6/2002 | Briquet et al. |
| 6,437,083 B1 | 8/2002 | Brack et al. |
| 6,448,334 B1 | 9/2002 | Verhoogt et al. |
| 6,458,468 B1 | 10/2002 | Moskala et al. |
| 6,504,002 B1 | 1/2003 | Karlik et al. |
| 6,559,272 B1 | 5/2003 | Jeon et al. |
| 6,573,328 B2 | 6/2003 | Kropp et al. |
| 6,599,994 B2 | 7/2003 | Shelby et al. |
| 6,600,080 B1 | 7/2003 | Nagamura et al. |
| 6,639,067 B1 | 10/2003 | Brinegar et al. |
| 6,656,577 B1 | 12/2003 | Adelman et al. |
| 6,669,980 B2 | 12/2003 | Hansen |
| 6,723,768 B2 | 4/2004 | Adams et al. |
| 6,733,716 B2 | 5/2004 | Belcher |
| 6,740,377 B2 | 5/2004 | Pecorini et al. |
| 6,773,653 B2 | 8/2004 | Miller et al. |

| | | | | | | |
|---|---|---|---|---|---|---|
| 6,818,293 | B1 | 11/2004 | Keep et al. | 2006/0270773 A1 | 11/2006 | Hale et al. |
| 6,818,730 | B2 | 11/2004 | Brandenburg et al. | 2006/0270806 A1 | 11/2006 | Hale |
| 6,846,440 | B2 | 1/2005 | Flynn et al. | 2007/0049667 A1 | 3/2007 | Kim et al. |
| 6,846,508 | B1 | 1/2005 | Colas et al. | 2007/0071930 A1 | 3/2007 | Shelby et al. |
| 6,896,966 | B2 | 5/2005 | Crawford et al. | 2008/0132738 A1 | 6/2008 | McCusker-Orth et al. |
| 6,908,650 | B2 | 6/2005 | Odorisio et al. | 2008/0154069 A1 | 6/2008 | McCusker-Orth et al. |
| 6,914,120 | B2 | 7/2005 | Germroth et al. | 2008/0221294 A1 | 9/2008 | O'Meadhra et al. |
| 6,919,489 | B1 | 7/2005 | McCusker-Orth | 2009/0123756 A1 | 5/2009 | Hashimoto et al. |
| 7,037,576 | B2 | 5/2006 | Willham et al. | | | |
| 7,048,978 | B2 | 5/2006 | Tanaka et al. | | | |

FOREIGN PATENT DOCUMENTS

| | | |
|---|---|---|
| 7,053,143 B2 | 5/2006 Mori et al. | |
| 7,122,661 B2 | 10/2006 Fleche et al. | DE 29 21 868 A1 12/1980 |
| 7,169,880 B2 | 1/2007 Shelby et al. | DE 197 27 709 6/1997 |
| 7,297,755 B2 | 11/2007 Shelby et al. | DE 198 11 773 A1 9/1999 |
| 7,354,628 B2 | 4/2008 Steube | EP 0 039 838 A1 11/1981 |
| 7,375,154 B2 | 5/2008 Stafford et al. | EP 0 273 144 5/1987 |
| 7,427,430 B2 | 9/2008 Rhee et al. | EP 0 282 277 9/1988 |
| 7,468,409 B2 | 12/2008 Pearson et al. | EP 0 372 846 6/1990 |
| 7,482,397 B2 | 1/2009 Pearson et al. | EP 0 544 008 A1 6/1993 |
| 2001/0029324 A1 | 10/2001 Walker et al. | EP 0 595 413 A1 5/1994 |
| 2001/0031805 A1 | 10/2001 Buhler | EP 0 698 631 2/1996 |
| 2001/0034419 A1 | 10/2001 Kanayama et al. | EP 0 714 764 A2 6/1996 |
| 2001/0044003 A1 | 11/2001 Gallucci et al. | EP 0 902 052 A1 3/1999 |
| 2002/0055586 A1 | 5/2002 Dalgewicz, III et al. | EP 0 930 531 A1 7/1999 |
| 2002/0128357 A1 | 9/2002 Goossens et al. | EP 1 035 167 A 9/2000 |
| 2002/0132963 A1 | 9/2002 Quillen | EP 1 066 825 A1 1/2001 |
| 2002/0137856 A1 | 9/2002 Andrews et al. | EP 1 674 496 A1 6/2006 |
| 2002/0188092 A1 | 12/2002 Moskala et al. | FR 1278284 12/1961 |
| 2002/0198297 A1 | 12/2002 Odorisio et al. | FR 1291273 5/1965 |
| 2003/0032737 A1 | 2/2003 Andrews et al. | FR 1432471 2/1966 |
| 2003/0060546 A1 | 3/2003 Moskala et al. | FR 1434658 2/1966 |
| 2003/0075516 A1 | 4/2003 Rothman et al. | FR 2112400 6/1972 |
| 2003/0077546 A1 | 4/2003 Donovan et al. | GB 962913 7/1964 |
| 2003/0135015 A1 | 7/2003 Fujimaki et al. | GB 1041651 9/1966 |
| 2003/0139497 A1 | 7/2003 Odorisio et al. | GB 1044015 9/1966 |
| 2003/0149177 A1 | 8/2003 Andrews et al. | GB 1047043 11/1966 |
| 2003/0169514 A1 | 9/2003 Bourdelais et al. | GB 1090241 11/1967 |
| 2003/0187151 A1 | 10/2003 Adams et al. | GB 1130558 10/1968 |
| 2003/0195295 A1 | 10/2003 Mahood et al. | GB 1 278 284 6/1972 |
| 2003/0221716 A1 | 12/2003 Olson | GB 1364732 8/1974 |
| 2003/0229181 A1 | 12/2003 Hariharan et al. | GB 2216919 A 10/1989 |
| 2004/0022526 A1 | 2/2004 Kuno et al. | JP 56-88440 A 12/1979 |
| 2004/0063864 A1 | 4/2004 Adams et al. | JP 03207743 9/1991 |
| 2004/0101687 A1 | 5/2004 Crawford et al. | JP 65-01040 2/1994 |
| 2004/0106707 A1 | 6/2004 Su et al. | JP 9-59371 A 4/1997 |
| 2004/0106767 A1 | 6/2004 Simon et al. | JP 11-222516 8/1999 |
| 2004/0108623 A1 | 6/2004 Deeter et al. | JP 2001-066701 8/1999 |
| 2004/0138381 A1 | 7/2004 Blasius et al. | JP 2000-352620 A 12/2000 |
| 2004/0145700 A1 | 7/2004 Miniutti et al. | JP 2001-098086 4/2001 |
| 2004/0164279 A1 | 8/2004 Stevenson et al. | JP 2001-214049 8/2001 |
| 2004/0202822 A1 | 10/2004 Bourdelais et al. | JP 2003292593 A 10/2003 |
| 2004/0214984 A1 | 10/2004 Keep et al. | JP 2004-058565 A 2/2004 |
| 2005/0008885 A1 | 1/2005 Blakely et al. | JP 2004-066624 A 3/2004 |
| 2005/0072060 A1 | 4/2005 Moncho et al. | JP 2004-067973 A 3/2004 |
| 2005/0075466 A1 | 4/2005 Oguro et al. | JP 2004-244497 A 9/2004 |
| 2005/0096453 A1 | 5/2005 Flynn et al. | JP 2004-292558 A 10/2004 |
| 2005/0101759 A1 | 5/2005 Odorisio et al. | JP 2005-254757 A 9/2005 |
| 2005/0113556 A1 | 5/2005 Strand et al. | JP 2007-069914 A 3/2007 |
| 2005/0119359 A1 | 6/2005 Shelby et al. | JP 2007-253491 A 10/2007 |
| 2005/0124779 A1 | 6/2005 Shelby et al. | KR 2001-089942 10/2001 |
| 2005/0181155 A1 | 8/2005 Share et al. | KR 2003-054611 7/2003 |
| 2005/0209435 A1 | 9/2005 Hirokane et al. | WO WO 97-01118 1/1997 |
| 2006/0004151 A1 | 1/2006 Shaikh et al. | WO WO 01-06981 2/2001 |
| 2006/0036012 A1 | 2/2006 Hayes et al. | WO WO 01-85824 A2 11/2001 |
| 2006/0094858 A1 | 5/2006 Turner et al. | WO WO 02-055570 A1 7/2002 |
| 2006/0111481 A1 | 5/2006 Pearson et al. | WO WO 02-059207 8/2002 |
| 2006/0111519 A1 | 5/2006 Strand et al. | WO WO 2004-009146 A1 1/2004 |
| 2006/0135668 A1 | 6/2006 Hayes | WO WO 2004-039860 5/2004 |
| 2006/0146228 A1 | 7/2006 Sogo et al. | WO WO 2004-104077 12/2004 |
| 2006/0151907 A1 | 7/2006 Kashiwabara | WO WO 2004-106988 A2 12/2004 |
| 2006/0180560 A1 | 8/2006 Robinson | WO WO 2005-007735 A2 1/2005 |
| 2006/0197246 A1 | 9/2006 Hale et al. | WO WO 2005-026241 A1 3/2005 |
| 2006/0199904 A1 | 9/2006 Hale et al. | WO WO 2006-025827 3/2006 |
| 2006/0199919 A1 | 9/2006 Hale et al. | WO WO 2006-127755 A2 11/2006 |
| 2006/0228507 A1 | 10/2006 Hale et al. | WO WO 2006-127831 A1 11/2006 |
| 2006/0234073 A1 | 10/2006 Hale et al. | WO WO 2007-053434 A1 5/2007 |
| 2006/0235167 A1 | 10/2006 Hale et al. | WO WO 2007-053548 A2 5/2007 |
| 2006/0241325 A1 | 10/2006 Komplin et al. | WO WO 2007-053549 A1 5/2007 |
| 2006/0247388 A1 | 11/2006 Hale et al. | WO WO 2007/0123631 5/2007 |

OTHER PUBLICATIONS

"Plastic Additives Handbook," 5th Edition, 2001, pp. 98-108 and pp. 109-112 (Hanser Gardner Publications, Inc., Cincinnati, OH.

Scheirs, John, et al., "Modern Polyesters: Chemistry and Technology of Polyesters and Copolyesters," Technology & Engineering, 2003, p. 287.

English language Abstract of JP 02-305816 from Patent Abstracts of Japan, Dec. 19, 1990.

English language translation of Belgian Patent No. BE 615,850, Apr. 13, 1962.

English language translation of French Patent No. FR 1,432,471, Feb. 7, 1966.

English language translation of French Patent No. FR 1,434,658, Feb. 28, 1966.

U.S. Appl. No. 11/390,555, filed Mar. 28, 2006, Emmett Dudley Crawford, et al.

U.S. Appl. No. 11/390,563, filed Mar. 28, 2006, Emmett Dudley Crawford, et al.

U.S. Appl. No. 11/390,629, filed Mar. 28, 2006, Emmett Dudley Crawford, et al.

U.S. Appl. No. 11/390,630, filed Mar. 28, 2006, Emmett Dudley Crawford, et al.

U.S. Appl. No. 11/390,631, filed Mar. 28, 2006, Emmett Dudley Crawford, et al.

U.S. Appl. No. 11/390,654, filed Mar. 28, 2006, Emmett Dudley Crawford, et al.

U.S. Appl. No. 11/390,655, filed Mar. 28, 2006, Emmett Dudley Crawford, et al.

U.S. Appl. No. 11/390,671, filed Mar. 28, 2006, Emmett Dudley Crawford, et al.

U.S. Appl. No. 11/390,672, filed Mar. 28, 2006, Emmett Dudley Crawford, et al.

U.S. Appl. No. 11/390,722, filed Mar. 28, 2006, Emmett Dudley Crawford, et al.

U.S. Appl. No. 11/390,750, filed Mar. 28, 2006, Emmett Dudley Crawford, et al.

U.S. Appl. No. 11/390,751, filed Mar. 28, 2006, Emmett Dudley Crawford, et al.

U.S. Appl. No. 11/390,752, filed Mar. 28, 2006, Emmett Dudley Crawford, et al.

U.S. Appl. No. 11/390,773, filed Mar. 28, 2006, Emmett Dudley Crawford, et al.

U.S. Appl. No. 11/390,793, filed Mar. 28, 2006, Emmett Dudley Crawford, et al.

U.S. Appl. No. 11-390,794, filed Mar. 28, 2006, Emmett Dudley Crawford, et al.

U.S. Appl. No. 11/390,809, filed Mar. 28, 2006, Wesley Raymond Hale, et al.

U.S. Appl. No. 11/390,811, filed Mar. 28, 2006, Emmett Dudley Crawford, et al.

U.S. Appl. No. 11/390,812, filed Mar. 28, 2006, Wesley Raymond Hale, et al.

U.S. Appl. No. 11/390,814, filed Mar. 28, 2006, Emmett Dudley Crawford, et al.

U.S. Appl. No. 11/390,826, filed Mar. 28, 2006, Emmett Dudley Crawford, et al.

U.S. Appl. No. 11/390,827, filed Mar. 28, 2006, Emmett Dudley Crawford, et al.

U.S. Appl. No. 11/390,836, filed Mar. 28, 2006, Emmett Dudley Crawford, et al.

U.S. Appl. No. 11/390,846, filed Mar. 28, 2006, Wesley Raymond Hale, et al.

U.S. Appl. No. 11/390,847, filed Mar. 28, 2006, Emmett Dudley Crawford, et al.

U.S. Appl. No. 11/390,853, filed Mar. 28, 2006, Emmett Dudley Crawford, et al.

U.S. Appl. No. 11/390,858, filed Mar. 28, 2006, Emmett Dudley Crawford, et al.

U.S. Appl. No. 11/390,864, filed Mar. 28, 2006, Wesley Raymond Hale, et al.

U.S. Appl. No. 11/390,865, filed Mar. 28, 2006, Emmett Dudley Crawford, et al.

U.S. Appl. No. 11/390,882, filed Mar. 28, 2006, Emmett Dudley Crawford, et al.

U.S. Appl. No. 11/390,883, filed Mar. 28, 2006, Thomas Joseph Pecorini, et al.

U.S. Appl. No. 11/390,908, filed Mar. 28, 2006, Wesley Raymond Hale, et al.

U.S. Appl. No. 11/391,063, filed Mar. 28, 2006, Emmett Dudley Crawford, et al.

U.S. Appl. No. 11/391,124, filed Mar. 28, 2006, Wesley Raymond Hale, et al.

U.S. Appl. No. 11/391,125, filed Mar. 28, 2006, Emmett Dudley Crawford, et al.

U.S. Appl. No. 11/391,137, filed Mar. 28, 2006, Emmett Dudley Crawford, et al.

U.S. Appl. No. 11/391,156, filed Mar. 28, 2006, Emmett Dudley Crawford, et al.

U.S. Appl. No. 11/391,485, filed Mar. 28, 2006, Emmett Dudley Crawford, et al.

U.S. Appl. No. 11/391,495, filed Mar. 28, 2006, Emmett Dudley Crawford, et al.

U.S. Appl. No. 11/391,505, filed Mar. 28, 2006, Emmett Dudley Crawford, et al.

U.S. Appl. No. 11/391,565, filed Mar. 28, 2006, Emmett Dudley Crawford, et al.

U.S. Appl. No. 11/391,571, filed Mar. 28, 2006, Emmett Dudley Crawford, et al.

U.S. Appl. No. 11/391,576, filed Mar. 28, 2006, Emmett Dudley Crawford, et al.

U.S. Appl. No. 11/391,642, filed Mar. 28, 2006, Emmett Dudley Crawford, et al.

U.S. Appl. No. 11/391,659, filed Mar. 28, 2006, Emmett Dudley Crawford, et al.

U.S. Appl. No. 11/588,524, filed Oct. 27, 2006, Emmett Dudley Crawford, et al.

U.S. Appl. No. 11/588,458, filed Oct. 27, 2006, Emmett Dudley Crawford, et al.

U.S. Appl. No. 11/588,907, filed Oct. 27, 2006, Emmett Dudley Crawford, et al.

U.S. Appl. No. 11/588,527, filed Oct. 27, 2006, Emmett Dudley Crawford, et al.

U.S. Appl. No. 11/588,906, filed Oct. 27, 2006, Ted Calvin Germroth, et al.

U.S. Appl. No. 11/588,883, filed Oct. 27, 2006, Ted Calvin Germroth, et al.

U.S. Appl. No. 11/588,554, filed Oct. 27, 2006, Emmett Dudley Crawford, et al.

U.S. Appl. No. 11/635,434, filed Dec. 7, 2006, Emmett Dudley Crawford.

U.S. Appl. No. 11/635,433, filed Dec. 7, 2006, Emmett Dudley Crawford.

U.S. Appl. No. 11/439,062, filed May 23, 2006, Wesley Raymond Hale, et al.

U.S. Appl. No. 11/439,340, filed May 23, 2006, Wesley Raymond Hale.

U.S. Appl. No. 11/706,476, filed Feb. 14, 2007, Leslie Shane Moody, et al.

U.S. Appl. No. 11/706,791, filed Feb. 14, 2007, Leslie Shane Moody, et al.

U.S. Appl. No. 12/091,568, filed Apr. 25, 2008, Emmett Dudley Crawford, et al.

U.S. Appl. No. 12/091,566, filed Apr. 25, 2008, Emmett Dudley Crawford, et al.

U.S. Appl. No. 12/091,570, filed Apr. 25, 2008, Ted Calvin Germroth, et al.

U.S. Appl. No. 12/091,572, filed Apr. 25, 2008, Ted Calvin Germroth, et al.

U.S. Appl. No. 12/294,690, filed Sep. 26, 2008, Ted Calvin Germroth et al.

U.S. Appl. No. 12/294,686, filed Sep. 26, 2008, Ted Calvin Germroth et al.

U.S. Appl. No. 12/274,692, filed Nov. 20, 2008, Thomas Joseph Pecorini et al.

U.S. Appl. No. 12/338,453, filed Dec. 18, 2008, Emmett Dudley Crawford, et al.
U.S. Appl. No. 12/361,779, filed Jan. 29, 2009, Emmett Dudley Crawford.
U.S. Appl. No. 12/365,515, filed Feb. 4, 2009, Emmett Dudley Crawford.
Chapter 4—*Processing of Plastics in "Plastics Engineering, 3rd ed"*, R.J. Crawford, Butterworth-Heinemann Publisher, 1998, Oxford, England, pp. 245-342.
Fox equation (T.G. Fox, Session J, Bull. Am. Phys. Soc., 1, 123 (1956)).
*The Technology of Plasticizers*, by J. Kern Sears and Joseph R Darby, published by Society of Plastic Engineers—Wiley and Sons, New York, 1982; pp. 136-139.
Coleman et al., "Polymer Reviews—A Practical Guide to Polymer Miscibility," *Polymer* 31, pp. 1187-1203 (1990).
"*Hansen Solubility Parameters, a Users Handbook*", by Charles M. Hansen, Chapter 1, CRC Press, 2000, pp. 1-24.
Martinez et al., "*Phase Behavior and Mechanical Properties of Injection Molded Poly (Ethylene Terephthalate )—Polyarylate Blends*"; Journal of Applied Polymer Science, John Wiley and Sons Inc. New York, US, vol. 45, No. 7, Jul. 5, 1992, p. 1135-1143.
Won Ho Jo et al. : :*Miscibility of poly(ether imide)-poly(ethylene terephthalate)* blends; Polymer Bulletin, Springer, Heidelberg, DE, vol. 33, No. 1, Jun. 1, 1994, pp. 113-118 (1994).
Anonymous: "*Poly (ethylene naphthalenedicarboxylate)-polyetherimide blends*" Research Disclosure, Mason Publications, Hampshire, GB, vol. 283, No. 38, Nov. 1987.
ASTM D1525—06, *Standard Test Method for Vicat Softening Temperature of Plastics*, Mar. 15, 2006.
ASTM D648—06, *Standard Test Method for Deflection Temperature of Plastics Under Flexural Load in the Edgewise Position*, Mar. 15, 2006.
ASTM D256—06, *Standard Test Methods for Determining the Izod Pendulum Impact Resistance of Plastics*, Mar. 15, 2006.
ASTM D790—03, *Standard Test Methods for Flexural Properties of Unreinforced and Reinforced Plastics and Electrical Insulating Materials*, Mar. 10, 2003.
ASTM D638—03, *Standard Test Method for Tensile Properties of Plastics*, Dec. 1, 2003.
ASTM D3418—03, *Transition Temperatures and Enthalpies of Fusion and Crystallization of Polymers by Differential Scanning Calorimetry*, Dec. 1, 2003.
Database WPI, Section Ch, Week 200536, Derwent Publications Ltd., London, GB; Class A23, AN 2005-355258, XP002396922 & WO 2005-030833 A1 (KANEBO Ltd) Apr. 7, 2005 abstract.
Shearer, N. H., "T18-Type 1 Polyesters," Mar. 1966, SPE Annual Technical Conference and Exhibition, XP009080224.
Gachter, Muller, "Taschenbuch der Kunststoff-Additive," 1990, Carl Hanser Verlag Munchen Wien, XP02450422, pp. 96-97.
Gachter, Muller, "Kunstoff-Additive," 1990, Carl Hanser Verlag Munchen Wien, XP 02449987, pp. 96-99.
Brown, R., "Taschenbuch Kunstoff-Additive", 1990, Carl Hanswer Verlag Munchen Wiel, XP002455247, pp. 361-363.
Chang, S. et al., "Effect of Stabilizers on the Preparation of Poly(ethylene Terephthalate)", Journal of Polymer Science, Polymer Chemistry Edition, 1982, vol. 20, pp. 2053-2061, John Wiley & Sons, Inc.
USPTO Office Action dated Mar. 11, 2008 for copending U.S. Appl. No. 11/391,642.
USPTO Office Action dated Mar. 24, 2008 for copending U.S. Appl. No. 11/390,908.
USPTO Office Action dated Apr. 15, 2008 for copending U.S. Appl. No. 11/390,629.
USPTO Office Action dated Apr. 16, 2008 for copending U.S. Appl. No. 11/390,751.
USPTO Office Action dated Apr. 17, 2008 for copending U.S. Appl. No. 11/390,814.
USPTO Office Action dated Jun. 3, 2008 for copending U.S. Appl. No. 11/391,063.
USPTO Office Action dated Sep. 10, 2008 for copending U.S. Appl. No. 11/390,752.
USPTO Office Action dated Sep. 10, 2008 for copending U.S. Appl. No. 11/390,794.
USPTO Office Action dated Sep. 19, 2008 for copending U.S. Appl. No. 11/391,565.
USPTO Office Action dated Oct. 2, 2008 for copending U.S. Appl. No. 11/390,671.
USPTO Office Action dated Sep. 24, 2008 for copending U.S. Appl. No. 11/390,631.
USPTO Office Action dated Oct. 1, 2008 for copending U.S. Appl. No. 11/390,655.
USPTO Office Action dated Sep. 29, 2008, for copending U.S. Appl. No. 11/391,137.
USPTO Office Action dated Sep. 9, 2008 for copending U.S. Appl. No. 11/391,571.
USPTO Office Action dated Oct. 22, 2008 for copending U.S. Appl. No. 11/391,125.
USPTO Office Action dated Oct. 20, 2008 for copending U.S. Appl. No. 11/390,672.
USPTO Office Action dated Oct. 8, 2008 for copending U.S. Appl. No. 11/390,853.
USPTO Office Action dated Oct. 9, 2008 for copending U.S. Appl. No. 11/391,505.
USPTO Notice of Allowance dated Oct. 7, 2008 for copending U.S. Appl. No. 11/390,908.
USPTO Office Action dated Oct. 14, 2008 for copending U.S. Appl. No. 11/390,811.
USPTO Office Action dated Oct. 22, 2008 for copending U.S. Appl. No. 11/390,750.
USPTO Office Action dated Oct. 22, 2008 for copending U.S. Appl. No. 11/390,865.
USPTO Office Action dated Oct. 14, 2008 for copending U.S. Appl. No. 11/390,654.
USPTO Office Action dated Oct. 20, 2008 for copending U.S. Appl. No. 11/390,836.
Copending, U.S. Appl. No. 12/254,894, filed on Oct. 21, 2008, Gary Michael Stack, et al.
Copending U.S. Appl. No. 12/390,694, filed on Feb. 23, 2009, Gary Michael Stack.
USPTO Office Action dated Oct. 29, 2008 for copending U.S. Appl. No. 11/390,955.
USPTO Notice of Allowance dated Nov. 3, 2008 for copending U.S. Appl. No. 11/391,642.
USPTO Office Action dated Nov. 3, 2008 for copending U.S. Appl. No. 11/391,485.
USPTO Office Action dated Oct. 29, 2008 for copending U.S. Appl. No. 11/390,864.
USPTO Office Action dated Oct. 30, 2008 for copending U.S. Appl. No. 11/391,495.
USPTO Office Action dated Oct. 31, 2008 for copending U.S. Appl. No. 11/391,156.
USPTO Office Action dated Nov. 3, 2008 for copending U.S. Appl. No. 11/390,883.
USPTO Office Action dated Dec. 19, 2008 for copending U.S. Appl. No. 11/390,751.
USPTO Office Action dated Dec. 31, 2008 for copending U.S. Appl. No. 11/390,827.
USPTO Office Action dated Dec. 31, 2008 for copending U.S. Appl. No. 11/390,826.
USPTO Office Action dated Nov. 14, 2008 for copending U.S. Appl. No. 11/390,630.
USPTO Office Action dated Dec. 19, 2008 for copending U.S. Appl. No. 11/391,576.
USPTO Office Action dated Dec. 19, 2008 for copending U.S. Appl. No. 11/390,629.
USPTO Office Action dated Dec. 31, 2008 for copending U.S. Appl. No. 11/390,773.
USPTO Office Action dated Dec. 12, 2008 for copending U.S. Appl. No. 11/391,063.
USPTO Office Action dated Dec. 19, 2008 for copending U.S. Appl. No. 11/390,814.
USPTO Office Action dated Dec. 31, 2008 for copending U.S. Appl. No. 11/390,722.
USPTO Office Action dated Nov. 14, 2008 for copending U.S. Appl. No. 11/390,882.

USPTO Office Action dated Jan. 29, 2009 for copending U.S. Appl. No. 11/588,524.
USPTO Office Action dated Jan. 30, 2009 for copending U.S. Appl. No. 11/588,458.
USPTO Office Action dated Feb. 2, 2009 for copending U.S. Appl. No. 11/390,853.
USPTO Office Action dated Jan. 21, 2009 for copending U.S. Appl. No. 11/390,847.
USPTO Office Action dated Jan. 12, 2009 for copending U.S. Appl. No. 11/390,858.
USPTO Office Action dated Jan. 26, 2009 for copending U.S. Appl. No. 11/391,659.
USPTO Office Action dated Jan. 26, 2009 for copending U.S. Appl. No. 11/588,554.
USPTO Office Action dated Feb. 3, 2009 for copending U.S. Appl. No. 11/391,505.
USPTO Office Action dated Feb. 10, 2009 for copending U.S. Appl. No. 11/390,865.
USPTO Office Action dated Feb. 12, 2009 for copending U.S. Appl. No. 11/439,062.
USPTO Office Action dated Feb. 13, 2009 for copending U.S. Appl. No. 11/439,340.
USPTO Office Action dated Feb. 25, 2009 for copending U.S. Appl. No. 11/588,907.
USPTO Office Action dated Feb. 25, 2009 for copending U.S. Appl. No. 11/588,527.
USPTO Office Action dated Feb. 27, 2009 for copending U.S. Appl. No. 11/390,955.
USPTO Office Action dated Feb. 25, 2009 for copending U.S. Appl. No. 11/588,906.
USPTO Office Action dated Feb. 25, 2009 for copending U.S. Appl. No. 11/588,883.
USPTO Office Action dated Mar. 5, 2009 for copending U.S. Appl. No. 11/390,864.
USPTO Office Action dated Mar. 6, 2009 for copending U.S. Appl. No. 11/391,156.
USPTO Office Action dated Feb. 25, 2009 for copending U.S. Appl. No. 11/390,811.
USPTO Office Action dated Feb. 27, 2009 for copending U.S. Appl. No. 11/390,654.
USPTO Office Action dated Feb. 27, 2009 for copending U.S. Appl. No. 11/390,836.
USPTO Office Action dated Mar. 13, 2009 for copending U.S. Appl. No. 11/390,883.
USPTO Office Action dated Mar. 11, 2009 for copending U.S. Appl. No. 11/390,630.
USPTO Office Action dated Mar. 9, 2009 for copending U.S. Appl. No. 11/391,495.
USPTO Office Action dated Mar. 9, 2009 for copending U.S. Appl. No. 11/390,750.
USPTO Office Action dated Mar. 16, 2009 for copending U.S. Appl. No. 11/390,882.
USPTO Office Action dated Apr. 27, 2009 for copending U.S. Appl. No. 11/390,655.
USPTO Office Action dated Apr. 27, 2009 for copending U.S. Appl. No. 11/391,137.
USPTO Office Action dated Mar. 16, 2009 for copending U.S. Appl. No. 11/391,485.
USPTO Office Action dated Apr. 15, 2009 for copending U.S. Appl. No. 12/091,566.
USPTO Notice of Allowance dated Apr. 13, 2009 for copending U.S. Appl. No. 11/391,063.
USPTO Office Action dated Apr. 16, 2009 for copending U.S. Appl. No. 12/091,570.
USPTO Office Action dated Apr. 17, 2009 for copending U.S. Appl. No. 11/390,671.
USPTO Office Action dated Apr. 17, 2009 for copending U.S. Appl. No. 11/391,565.
USPTO Office Action dated Apr. 20, 2009 for copending U.S. Appl. No. 11/390,631.
USPTO Office Action dated Mar. 31, 2009 for copending U.S. Appl. No. 11/390,563.
USPTO Office Action dated Apr. 2, 2009 for copending U.S. Appl. No. 11/390,793.
USPTO Office Action dated Mar. 23, 2009 for copending U.S. Appl. No. 11/390,752.
USPTO Office Action dated Mar. 23, 2009 for copending U.S. Appl. No. 11/390,794.
USPTO Office Action dated May 13, 2009 for copending U.S. Appl. No. 12/361,779.
USPTO Office Action dated May 13, 2009 for copending U.S. Appl. No. 12/365,515.
USPTO Office Action dated May 21, 2009 for copending U.S. Appl. No. 11/706,476.
USPTO Office Action dated May 22, 2009 for copending U.S. Appl. No. 11/706,791.
USPTO Office Action dated May 18, 2009 for copending U.S. Appl. No. 11/391,505.
USPTO Office Action dated Apr. 14, 2009 for copending U.S. Appl. No. 11/635,434.
USPTO Office Action dated Apr. 14, 2009 for copending U.S. Appl. No. 11/635,433.
USPTO Office Action dated May 18, 2009 for copending U.S. Appl. No. 11/390,846.
USPTO Office Action dated Jun. 11, 2009 for copending U.S. Appl. No. 11/390,809.
USPTO Office Action dated Jul. 2, 2009 for copending U.S. Appl. No. 11/390,827.
USPTO Office Action dated Aug. 7, 2009 for copending U.S. Appl. No. 11/390,773.
USPTO Office Action dated Aug. 27, 2009 for copending U.S. Appl. No. 11/390,826.
USPTO Office Action dated Aug. 10, 2009 for copending U.S. Appl. No. 11/390,722.
Dixon, E.R. et al., "The Inter-Relation of Some Mechanical Properties with Molecular Weight and Crystallinity in Poly(ethylene terephthalate)", 1968, pp. 464-470, Journal of Materials Science, vol. 3.
USPTO Office Action dated Sep. 4, 2009, for copending U.S. Appl. No. 11/391,124.
USPTO Office Action dated Sep. 10, 2009, for copending U.S. Appl. No. 11/390,812.
New Copending U.S. Appl. No. 12/479,893 filed Jun. 8, 2009, Emmett Dudley Crawford, et al.
USPTO Office Action dated Sep. 14, 2009 for copending U.S. Appl. No. 11/391,576.
Ellis, Thomas S., "Miscibility of Polyamide Blends: Effects of Configuration," 1995, Polymer, vol. 36, Issue 20, pp. 3919-3926.
Buschow, K.H.J., et al., "Packaging: Papers for Sacks and Bags," 2001, Encyclopedia of Materials: Science and Technology, vol. 8, Elsevier, pp. 6646-6652.
Coles, Richard, et al., "Food Packaging Technology," 2003, pp. 194-195 and 224-229, Blackwell Publishing.
Sajiki, Junko, et al., "Leaching of Bisphenol A (BPA) to Seawater from Polycarbonate Plastic and its Degradation by Reactive Oxygen Species," 2003, Chemosphere, 51, pp. 55-62.
USPTO Office Action dated Oct. 2, 2009 for copending U.S. Appl. No. 11/588,524.
USPTO Office Action dated Oct. 7, 2009 for copending U.S. Appl. No. 11/588,458.
USPTO Office Action dated Sep. 29, 2009 for copending U.S. Appl. No. 11/390,751.
USPTO Office Action dated Sep. 24, 2009 for copending U.S. Appl. No. 11/588,883.
USPTO Office Action dated Sep. 28, 2009 for copending U.S. Appl. No. 11/390,847.
USPTO Office Action dated Sep. 24, 2009 for copending U.S. Appl. No. 11/390,858.
USPTO Office Action dated Sep. 29, 2009 for copending U.S. Appl. No. 11/390,629.
USPTO Office Action dated Sep. 29, 2009 for copending U.S. Appl. No. 11/390,814.
USPTO Office Action dated Oct. 19, 2009 for copending U.S. Appl. No. 11/390,563.

USPTO Office Action dated Oct. 20, 2009 for copending U.S. Appl. No. 11/588,907.

USPTO Office Action dated Oct. 21, 2009 for copending U.S. Appl. No. 11/391,156.

Gupta, V.B. et al., "PET Fibers, Films, and Bottles: Section 5-7", Handbook of Thermoplastic Polyesters: Homopolymers, Copolymers, Blends, and Composites, 2005, pp. 362-388, Wiley InterScience.

USPTO Office Action dated Oct. 22, 2009 for copending U.S. Appl. No. 11/588,906.

USPTO Office Action dated Nov. 3, 2009 for copending U.S. Appl. No. 11/390,883.

USPTO Office Action dated Nov. 4, 2009 for copending U.S. Appl. No. 11/390,750.

USPTO Office Action dated Nov. 4, 2009 for copending U.S. Appl. No. 11/390,864.

USPTO Office Action dated Nov. 17, 2009 for copending U.S. Appl. No. 12/254,894.

USPTO Office Action dated Nov. 18, 2009 for copending U.S. Appl. No. 11/390,630.

USPTO Office Action dated Nov. 30, 2009 for copending U.S. Appl. No. 11/391,495.

Turner, S.R., et al., "Amorphous and Crystalline Polyesters based on 1,4-Cyclohexanedimethanol", Chapter 7, Modern Polyesters: Chemistry and Technology of Polyesters and Copolyesters, Edited by J. Sheirs and T.E. Long, 2003 John Wiley & Sons, Ltd., pp. 267-292.

USPTO Office Action dated Nov. 18, 2009 for copending U.S. Appl. No. 11/390,794.

USPTO Office Action dated Nov. 20, 2009 for copending U.S. Appl. No. 11/391,485.

USPTO Office Action dated Nov. 20, 2009 for copending U.S. Appl. No. 11/390,882.

USPTO Office Action dated Dec. 1, 2009 for copending U.S. Appl. No. 12/091,570.

USPTO Office Action dated Dec. 3, 2009 for copending U.S. Appl. No. 11/395,505.

USPTO Office Action dated Dec. 4, 2009 for copending U.S. Appl. No. 12/091,566.

Zipper, Marcus D.,et al., "A Free Volume Study of Miscible Polyester Blends," 1995, pp. 127-136, Polymer International, vol. 36.

"APEC High-Heat Polycarbonate Resin," 2004, Bayer Material Science Product Information *Not Prior Art; Submitted for State of the Art*.

Lobo, Hubert et al, "Handbook of Plastics Analysis," 2003, pp. 20 and 21, Marcel Dekker, Inc.

USPTO Notice of Allowance dated Dec. 11, 2009 for copending U.S. Appl. No. 12/365,515.

USPTO Office Action dated Dec. 18, 2009 for copending U.S. Appl. No. 11/390,846.

Copending Application U.S. Appl. No. 12/639,324, filed Dec. 16, 2009.

USPTO Notice of Allowance dated Dec. 22, 2009 for copending U.S. Appl. No. 12/361,779.

USPTO Office Action dated Jan. 7, 2010 for copending U.S. Appl. No. 12/091,568.

USPTO Office Action dated Jan. 13, 2010 for copending U.S. Appl. No. 11/635,433.

USPTO Office Action dated Jan. 14, 2010 for copending U.S. Appl. No. 11/390,809.

USPTO Notice of Allowance dated Jan. 27, 2010 for copending U.S. Appl. No. 11/635,434.

USPTO Office Action dated Mar. 11, 2010, for copending U.S. Appl. No. 11/391,124.

Copending Application U.S. Appl. No. 12/724,492, filed Mar. 16, 2010.

Copending Application U.S. Appl. No. 12/724,480, filed Mar. 16, 2010.

Copending Application U.S. Appl. No. 12/724,468, filed Mar. 16, 2010.

USPTO Office Action dated Mar. 19, 2010, for copending U.S. Appl. No. 11/588,527.

USPTO Notice of Allowance dated Mar. 24, 2010 for copending U.S. Appl. No. 11/391,565.

USPTO Office Action dated Mar. 29, 2010 for copending U.S. Appl. No. 11/390,812.

USPTO Notice of Allowance dated Apr. 15, 2010 for copending U.S. Appl. No. 11/391,505.

USPTO Office Action dated Apr. 19, 2010 for copending U.S. Appl. No. 12/724,480.

USPTO Office Action dated Apr. 21, 2010 for copending U.S. Appl. No. 12/724,468.

USPTO Office Action dated Apr. 21, 2010 for copending U.S. Appl. No. 12/724,492.

USPTO Office Action dated May 6, 2010 for copending U.S. Appl. No. 12/254,894.

New copending U.S. Appl. No. 12/784,193 filed on May 20, 2010, Emmett Dudley Crawford, et al.

USPTO Notice of Allowance dated May 13, 2010 for copending U.S. Appl. No. 11/390,629.

USPTO Notice of Allowance dated May 13, 2010 for copending U.S. Appl. No. 11/390,751.

USPTO Notice of Allowance dated May 21, 2010 for copending U.S. Appl. No. 11/391,156.

USPTO Notice of Allowance dated May 26, 2010 for copending U.S. Appl. No. 11/391,495.

USPTO Notice of Allowance dated Jun. 24, 2010 for copending U.S. Appl. No. 11/391,576.

USPTO Office Action dated Jun. 24, 2010 for copending U.S. Appl. No. 11/390,846.

USPTO Office Action dated Jul. 8, 2010 for copending U.S. Appl. No. 11/390,809.

USPTO Notice of Allowance dated Jul. 8, 2010 for copending U.S. Appl. No. 11/390,630.

USPTO Notice of Allowance dated Jul. 8, 2010 for copending U.S. Appl. No. 11/390,883.

USPTO Office Action dated Jul. 12, 2010 for copending U.S. Appl. No. 11/390,794.

Notice of Allowance dated Jul. 13, 2010 for copending U.S. Appl. No. 11/391,505.

USPTO Office Action dated Jul. 22, 2010 for copending U.S. Appl. No. 12/479,893.

USPTO Notice of Allowance dated Jul. 22, 2010 for copending U.S. Appl. No. 11/391,485.

USPTO Notice of Allowance dated Aug. 3, 2010 for copending U.S. Appl. No. 11/390,864.

USPTO Office Action dated Aug. 6, 2010 for copending U.S. Appl. No. 11/773,275.

New copending application U.S. Appl. No. 12/853,717, filed Aug. 10, 2010, Emmett Dudley Crawford, et al.

USPTO Notice of Allowance dated Aug. 11, 2010 for copending U.S. Appl. No. 11/390,631.

USPTO Notice of Allowance dated Sep. 2, 2010 for copending U.S. Appl. No. 11/390,811.

USPTO Office Action dated Sep. 2, 2010 for copending U.S. Appl. No. 11/391,124.

New copending application U.S. Appl. No. 12/888,648, filed Sep. 23, 2010, Thomas Joseph Pecorini et al.

USPTO Office Action dated Oct. 5, 2010 for copending U.S. Appl. No. 11/390,655.

New copending application U.S. Appl. No. 12/900,060, filed Oct. 7, 2010, Thomas Joseph Pecorini, et al.

USPTO Office Action dated 10-8-10 for copending U.S. Appl. No. 11/390,812.

USPTO Notice of Allowance dated Oct. 28, 2010 for copending U.S. Appl. No. 11/390,827.

USPTO Office Action dated Oct. 27, 2010 for copending U.S. Appl. No. 12/294,690.

New Copending Application U.S. Appl. No. 12/900,060, filed Oct. 7, 2010, Joseph Thomas Pecorini.

USPTO Notice of Allowance dated Oct. 14, 2010 for copending U.S. Appl. No. 11/390,722.

USPTO Notice of Allowance dated Nov. 2, 2010 for copending U.S. Appl. No. 12/724,480.

USPTO Notice of Allowance dated Nov. 4, 2010 for copending U.S. Appl. No. 12/724,468.

USPTO Notice of Allowance dated Nov. 4, 2010 for copending U.S. Appl. No. 11/390,955.
USPTO Office Action dated Nov. 4, 2010 for copending U.S. Appl. No. 12/294,686.
USPTO Notice of Allowance dated Nov. 4, 2010 for copending U.S. Appl. No. 11/390,826.
USPTO Office Action dated Oct. 27, 2010 for copending U.S. Appl. No. 11/390,836.
USPTO Notice of Allowance dated Nov. 23, 2010 for copending U.S. Appl. No. 11/390,563.
New copending application U.S. Appl. No. 12/943,217, filed Nov. 10, 2010, Emmett Dudley Crawford et al.
New copending application U.S. Appl. No. 12/963,698, filed Dec. 9, 2010.
New copending application U.S. Appl. No. 12/963,703, filed Dec. 9, 2010.
New copending application U.S. Appl. No. 13/007,838, filed Jan. 17, 2011, Emmett Dudley Crawford et al.
USPTO Office Action dated Jan. 24, 2011 for copending U.S. Appl. No. 11/773,275.
New copending application U.S. Appl. No. 13/016,147, filed Jan. 28, 2011, Emmett Dudley Crawford, et al.
New copending application U.S. Appl. No. 13/017,069, filed Jan. 31, 2011, Emmett Dudley Crawford, et al.
New Copending application U.S. Appl. No. 13/017,352, filed an. 31, 2011, Emmett Dudley Crawford, et al.
USPTO Office Action dated Jan. 25, 2011 for copending U.S. Appl. No. 12/853,717.
Al-Malaika, S., "Stabilization", Encyclopedia of Polymer Science and Technology, vol. 4, 2001, pp. 179-229, John Wiley & Sons, Inc.
USPTO Notice of Allowance dated Jan. 26, 2011 for copending U.S. Appl. No. 11/390,858.
USPTO Office Action dated Feb. 2, 2011 for copending U.S. Appl. No. 11/390,655.
USPTO Office Action dated Mar. 17, 2011 for copending U.S. Appl. No. 12/479,893.
USPTO Notice of Allowance dated Mar. 17, 2011 for copending U.S. Appl. No. 11/391,137.
USPTO Office Action dated Feb. 14, 2011 for copending U.S. Appl. No. 12/294,690.
USPTO Notice of Allowance dated Feb. 18, 2011 for copending U.S. Appl. No. 11/390,809.
USPTO Notice of Allowance dated Feb. 17, 2011 for copending U.S. Appl. No. 11/390,812.
New Copending U.S. Appl. No. 13/097,701, filed Apr. 29, 2011, Michael Eugene Donelson, et al.
USPTO Office Action dated Jun. 2, 2011 for copending U.S. Appl. No. 12/338,453.
USPTO Office Action dated Jun. 16, 2011 for copending U.S. Appl. No. 12/390,694.
USPTO Notice of Allowance dated Aug. 12, 2011 for copending U.S. Appl. No. 11/390,752.
USPTO Office Action dated Jul. 19, 2011 for copending U.S. Appl. No. 11/390,794.
USPTO Notice of Allowance dated Jul. 21, 2011 for copending U.S. Appl. No. 11/390,671.
USPTO Notice of Allowance dated Aug. 3, 2011 for copending U.S. Appl. No. 11/390,655.
New copending U.S. Appl. No. 13/162,870, filed Jun. 17, 2011, Emmett Dudley Crawford, et al.
USPTO Office Action dated Jul. 7, 2011 for copending U.S. Appl. No. 11/588,906.
USPTO Office Action dated Jun. 22, 2011 for copending U.S. Appl. No. 12/091,570.
USPTO Office Action dated Jun. 8, 2011 for copending U.S. Appl. No. 11/588,883.
USPTO Office Action dated Aug. 17, 2011 for copending U.S. Appl. No. 12/274,692.
New copending application U.S. Appl. No. 13/215,511, filed Aug. 23, 2011, Emmett Dudley Crawford, et al.
USPTO Office Action dated Sep. 14, 2011 for copending U.S. Appl. No. 13/017,069.
USPTO Notice of Allowance dated Sep. 16, 2011 for copending U.S. Appl. No. 11/390,671.
USPTO Notice of Allowance dated Sep. 16, 2011 for copending U.S. Appl. No. 12/784,193.
USPTO Office Action dated Oct. 17, 2011 for copending U.S. Appl. No. 12/853,717.
USPTO Notice of Allowance dated Oct. 17, 2011 for copending U.S. Appl. No. 11/390,794.
USPTO Notice of Allowance dated Oct. 25, 2011 for copending U.S. Appl. No. 12/900,060.
USPTO Office Action dated Oct. 31, 2011 for copending U.S. Appl. No. 12/639,324.
USPTO Office Action dated Nov. 2, 2011 for copending U.S. Appl. No. 12/479,893.
USPTO Notice of Allowance dated Nov. 2, 2011 for copending U.S. Appl. No. 12/390,694.
USPTO Notice of Allowance dated Nov. 10, 2011 for copending U.S. Appl. No. 12/943,217.
USPTO Notice of Allowance dated Nov. 28, 2011 for copending U.S. Appl. No. 12/274,692.
New copending U.S. Appl. No. 13/330,052, filed Dec. 19, 2011, Kenny Randolph Parker, et al.
USPTO Notice of Allowance dated Dec. 20, 2011 for copending U.S. Appl. No. 12/390,694.
USPTO Office Action dated Dec. 21, 2011 for copending U.S. Appl. No. 12/091,570.
New copending application U.S. Appl. No. 13/348,677, filed Jan. 12, 2012, Emmett Dudley Crawford, et al.
USPTO Notice of Allowance dated Feb. 14, 2012 for copending U.S. Appl. No. 11/588,906.
New copending U.S. Appl. No. 13/398,262, filed on Feb. 26, 2012, Emmett Dudley Crawford, et al.
Hasek, et al. Chemistry of Dimethylketone Dimer. Journal of Organic Chemistry, 1961, vol. 26, pp. 700-704.
Sprague et al., Hydrogenation and Hydrogenolysis of 1,3-Diketones. Journal of the American Chemical Society, 1934, vol. 56, pp. 2669-2675.
Coover, H. et al., "Copolyester Molding Compositions," Chemical Abstracts Service, XP002391844, 1970.
Bergen, R. L., Jr., "Stress Cracking of Rigid Thermoplastics," SPE Journal, pp. 667-669, Jun. 1962.
2866-43-5. Registry [>database>online].  Chemical Abstracts Services, a division of the American Chemical Society [retrieved on Nov. 6, 2006]. Retrieved from: SciFinder.
7128-64-5. Registry [>database>online ]. Chemical Abstracts Services, a division of the American Chemical Society [retrieved on Nov. 6, 2006]. Retrieved from SciFinder.
USPTO Office Action mailed Aug. 29, 2012 for copending U.S. Appl. No. 12/963,703.
USPTO Notice of Allowance mailed Nov. 5, 2012 for copending U.S. Appl. No. 12/963,703.
USPTO Office Action mailed Aug. 28, 2012 for copending U.S. Appl. No. 12/963,698.
International Search report and Written Opinion of the International Searching Authority mailed Feb. 14, 2012 for International Application No. PCT/US2011/062782.
nternational Search report and Written Opinion of the International Searching Authority mailed Jan. 16, 2012 for International Application No. PCT/US2011/062178.

Hydrogenation of 2,2,4,4-Tetraalkycyclobutane-1,3-dione
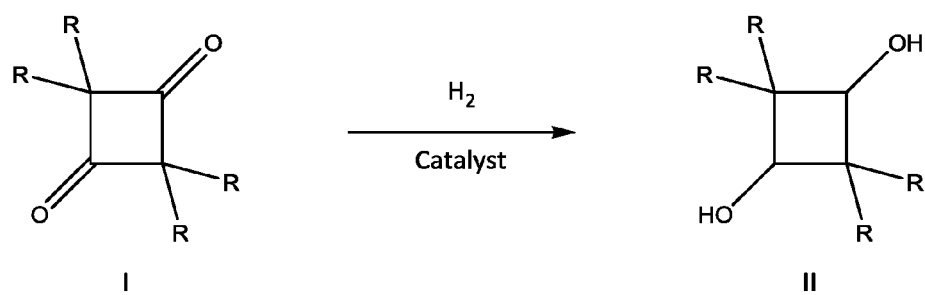

PROCESS FOR THE PREPARATION OF 2,2,4,4-TETRAALKYLCYCLOBUTANE-1,3-DIOLS

FIELD OF THE INVENTION

This invention pertains to a process for the preparation of a diol from the corresponding dione. In particular, this invention pertains a process for the preparation of a 2,2,4,4-tetraalkylcyclobutane-1,3-diol by hydrogenation of a 2,2,4,4-tetraalkylcyclobutane-1,3-dione in the presence of a catalyst comprising ruthenium deposited on a carbon nanotube support.

BACKGROUND OF THE INVENTION

Tetraalkylcyclobutane-1,3-diols can be important intermediates for producing a variety of polymeric materials which possess advantageous properties. For example, polyesters derived from dicarboxylic acids and 2,2,4,4-tetramethylcyclobutane-1,3-diol can possess higher glass transition temperatures, impact strength, weatherability, and hydrolytic stability in comparison to many polyesters prepared from other commonly-used diols. Tetraalkylcyclobutane-1,3-diols can be prepared by the catalytic hydrogenation of the corresponding 2,2,4,4-tetraalkylcyclobutane-1,3-dione (I) to the corresponding 2,2,4,4-tetramethylcyclobutane-1,3-diol (II), as illustrated in FIG. 1, in which R is an alkyl group.

Tetraalkylcyclobutanediols typically are produced by hydrogenation of the corresponding tetraalkylcyclobutanediones using a variety of catalysts such as, for example, nickel, ruthenium, and cobalt. For example, the hydrogenation of 2,2,4,4-tetramethylcyclobutane-1,3-dione to 2,2,4,4-tetramethylcyclobutane-1,3-diol can be carried out using nickel- or ruthenium-containing catalysts as described in U.S. Pat. Nos. 3,000,906, 3,190,928; 5,169,994; 5,258,556; and 2,936,324. The hydrogenation of 2,2,4,4-tetramethylcyclobutane-1,3-dione to 2,2,4,4-tetramethylcyclobutane-1,3-diol also can involve cobalt-containing catalysts. For example, U.S. Pat. Nos. 5,528,556 and 5,169,994 disclose that Raney cobalt is effective for hydrogenation of 2,2,4,4-tetramethylcyclobutane-1,3-dione to 2,2,4,4-tetramethylcyclobutane-1,3-diol.

It is known, however, that the nature of the catalyst support can influence catalyst activity and selectivity. For example, catalyst support materials such as alumina, titania, and silica-alumina can have acidic properties that, in turn, can catalyze side-reactions and reduce yield. In particular, 2,2,4,4-tetraalkylcyclobutanediones and their corresponding diols can be sensitive to acid catalysts, which can promote their decomposition into various by-products. Other attributes of the catalyst support, such as porosity, also can affect catalyst activity and selectivity. Some catalyst supports such as, for example, activated carbon, zeolites, and clays may be obtained or derived from natural sources and can have inconsistent properties and quality. There is a need, therefore, for new catalysts for the hydrogenation of 2,2,4,4-tetraalkylcyclobutane-1,3-diones and other sensitive substrates that show good activity and selectivity and can be prepared with consistent properties.

SUMMARY OF THE INVENTION

We have discovered that 2,2,4,4-tetraalkylcyclobutane-1,3-diols can be prepared by hydrogenating the corresponding 2,2,4,4-tetraalkylcyclobutane-1,3-dione in the present of ruthenium catalyst deposited on a carbon nanotube support. A general embodiment of our invention, therefore, is a process for the preparation of a 2,2,4,4-tetraalkylcyclobutane-1,3-diol, comprising contacting a 2,2,4,4-tetraalkylcyclobutane-1,3-dione having the formula (I):

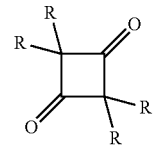

with hydrogen in the presence of a catalyst comprising about 0.1 to about 10 weight percent ruthenium, based on the total weight of the catalyst, deposited on a support comprising carbon nanotubes to form a 2,2,4,4-tetraalkylcyclobutane-1,3-diol having the formula (II):

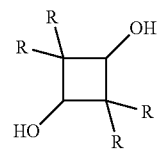

wherein R is a alkyl radical containing 1 to 8 carbon atoms. In general, the ruthenium/carbon nanotube catalysts utilized in the process of the invention can be prepared in high purity, with consistent properties, and exhibit high mechanical strength and thermal stability. Our novel process can produce 2,2,4,4-tetraalkylcyclobutane-1,3-diols in good yields and selectivities.

Our process may be used, in particular, for the preparation of 2,2,4,4-tetramethylcyclobutane-1,3-diol from 2,2,4,4-tetramethylcyclobutane-1,3-dione, and can be carried out under modest pressures and temperatures under continuous operating conditions. Thus, another aspect of the invention is a process for the preparation of 2,2,4,4-tetramethylcyclobutane-1,3-diol, comprising continuously feeding 2,2,4,4-tetramethylcyclobutane-1,3-dione, a solvent, and hydrogen to a hydrogenation zone comprising a hydrogenation catalyst comprising about 2 to about 8 weight percent ruthenium, based on the total weight of the catalyst, deposited on a support comprising carbon nanotubes at a pressure of about 2 to about 15 megapascals and a temperature of about 120 to about 200° C. and continuously recovering from the hydrogenation zone an effluent comprising 2,2,4,4-tetramethylcyclobutane-1,3-diol.

The process of the invention also can be used in combination with a process for the preparation of the 2,2,4,4-tetramethylcyclobutane-1,3-dione from isobutyric anhydride to provide an integrated process for 2,2,4,4-tetramethylcyclobutane-1,3-diol. Another embodiment of our invention, therefore, is a process for the preparation of 2,2,4,4-tetramethylcyclobutane-1,3-diol, comprising (1) feeding isobutyric anhydride to a pyrolysis zone produce a vapor effluent comprising dimethylketene, isobutyric acid and unreacted isobutyric anhydride;

(2) cooling the vapor effluent to condense isobutyric acid and isobutyric anhydride and separating the condensate from the dimethylketene vapor;

(3) feeding the dimethylketene vapor to an absorption zone wherein the dimethylketene vapor is contacted with and dissolved in a solvent to produce an effluent comprising a solution of dimethylketene in the solvent;

(4) feeding the absorption zone effluent to a dimerization zone wherein the effluent is heated to convert dimethylketene to 2,2,4,4-tetramethylcyclobutane-1,3-dione to produce an effluent comprising a solution of the 2,2,4,4-tetramethylcyclobutane-1,3-dione in the solvent; and (5) contacting the 2,2,4,4-tetramethylcyclobutane-1,3-dione with hydrogen in the presence of a catalyst comprising ruthenium deposited on a catalyst support comprising carbon nanotubes to form a 2,2,4,4-tetramethylcyclobutane-1,3-dione.

DESCRIPTION OF DRAWING

FIG. 1 represents the catalytic hydrogenation of 2,2,4,4-tetraalkylcyclobutane-1,3-dione into the corresponding 2,2,4,4-tetraalkylcyclobutane-1,3-diol.

DETAILED DESCRIPTION

The process provides for the preparation of 2,2,4,4-tetraalkylcyclobutane-1,3-diols such as, for example, 2,2,4,4-tetramethylcyclobutane-1,3-diol, by hydrogenation of the corresponding 2,2,4,4-tetraalkylcyclobutane-1,3-dione in the presence of a catalyst comprising ruthenium deposited on a carbon nanotube support. In a general embodiment, therefore, the instant invention provides a process for the preparation of a 2,2,4,4-tetraalkylcyclobutane-1,3-diol, comprising contacting a 2,2,4,4-tetraalkylcyclobutane-1,3-dione having the formula (I):

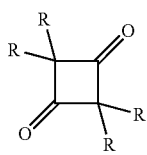

I with hydrogen in the presence of a catalyst comprising about 0.1 to about 10 weight percent ruthenium, based on the total weight of the catalyst, deposited on a support comprising carbon nanotubes to form a 2,2,4,4-tetraalkylcyclobutane-1,3-diol having the formula (II):

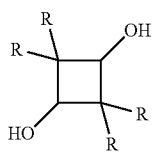

II wherein R is a alkyl radical containing 1 to 8 carbon atoms. Our hydrogenation process can produce tetraalkylcyclobutane-1,3-diols in good yields and selectivities. In one embodiment, for example, our process can be combined with a process for the preparation of the 2,2,4,4-tetramethylcyclobutane-1,3-dione from isobutyric anhydride to provide a novel and efficient process for 2,2,4,4-tetramethylcyclobutane-1,3-diol.

Unless otherwise indicated, all numbers expressing quantities of ingredients, properties such as molecular weight, reaction conditions, and so forth used in the specification and claims are to be understood as being modified in all instances by the term "about." Unless indicated to the contrary, the numerical parameters set forth in the following specification and attached claims are approximations that may vary depending upon the desired properties sought to be obtained by the present invention. At the very least, each numerical parameter should be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "C1 to C5 hydrocarbons", is intended to specifically include and disclose C1 and C5 hydrocarbons as well as C2, C3, and C4 hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in its respective testing measurements.

Also, it is to be understood that the mention of one or more process steps does not preclude the presence of additional process steps before or after the combined recited steps or intervening process steps between those steps expressly identified. Moreover, the lettering of process steps or ingredients is a convenient means for identifying discrete activities or ingredients and the recited lettering can be arranged in any sequence, unless otherwise indicated.

As used herein, the terms "tetraalkylcyclobutanediol," "tetraalkylcyclobutanedione," "tetramethylcyclobutanedione," and "tetramethylcyclobutanediol," are understood to be synonymous with the terms "2,2,4,4-tetraalkylcyclobutane-1,3-diol," "2,2,4,4-tetraalkylcyclobutane-1,3-dione," and "2,2,4,4-tetramethylcyclobutane-1,3-diol," respectively. The term "ruthenium" is understood to encompass all the various forms of the metal including elemental ruthenium itself as well as any compounds of ruthenium such as, for example, those containing oxygen, halide, trivalent nitrogen, carbon monoxide, hydrogen, carboxylates, and diones, either alone or in combination.

Our invention provides a process for the preparation of a 2,2,4,4-tetraalkylcyclobutane-1,3-diol having the formula (II) by hydrogenation of a 2,2,4,4-tetraalkylcyclobutane-1,3-dione having the formula (I) as illustrated in FIG. 1, wherein the R groups are identical, alkyl radicals having 1 to 8 carbon atoms. For example, the alkyl radicals represented by R can comprise 1 to 6 carbon atoms, 1 to 4 carbon atoms, or 1 to 2 carbon atoms. The alkyl radicals may be linear, branched or a combination of linear and branched alkyl radicals. Representative alkyl groups include, but are not limited to, methyl, ethyl, propyl, isopropyl, butyl, isobutyl, pentyl, isoamyl, hexyl, heptyl, and octyl. Some examples of 2,2,4,4-tetralkylcyclobutane-1,3-diones that can be hydrogenated in the process of the invention include 2,2,4,4-tetramethylcyclobutane-1,3-dione, 2,2,4,4-tetraethylcyclobutane-1,3-dione, 2,2,4,4-tetra-n-propylcyclobutane-1,3-dione, 2,2,4,4-tetraisopropylcyclobutane-1,3-dione, 2,2,4,4-tetra-n-butylcyclobutane-1,3-dione, 2,2,4,4-tetraisobutylcyclobutane-1,3-dione, 2,2,4,4-tetra-n-amylcyclobutane-1,3-dione, 2,2,4,4-tetraisoamylcyclobutane-1,3-dione, 2,2,4,4-tetra-n-hexylcyclobutane-1,3-dione, 2,2,4,4-tetra-2-ethylhexylcyclobutane-1,3-dione, 2,2,4,4-tetra-n-heptylcyclobutane-1,3-dione, and 2,2,4,4-tetra-n- octylcyclobutane-1,3-dione. For example, our invention may be illustrated with particular reference to the hydrogenation 2,2,4,4-tetramethylcyclobutane-1,3-dione to form 2,2,4,4-tetramethylcyclobutane-1,3-diol (i.e., R is methyl).

The starting 2,2,4,4-tetraalkylcyclobutane-1,3-dione can be contacted with hydrogen in the presence of a catalyst comprising ruthenium deposited on a carbon nanotube support. The source and purity of the hydrogen gas used in the processes of the present invention are not critical. The hydrogen gas used in the processes may comprise fresh hydrogen or a mixture of fresh hydrogen and recycle hydrogen. The hydrogen gas can be a mixture of hydrogen, optionally containing minor amounts, typically less than about 30 mole %, of components such as CO and $CO_2$, and inert gases, such as argon, nitrogen, or methane. Typically, the hydrogen gas comprises at least about 70 mole % of hydrogen. For example, the hydrogen gas can comprise at least 90 mole % or, in another example, at least 97 mole %, of hydrogen. The hydrogen gas can be obtained from any of the conventional sources well known in the art such as, for example, by partial oxidation or steam reforming of natural gas. Pressure swing absorption can be used if a high purity hydrogen gas is desired. If hydrogen gas recycle is utilized in the process, then the recycle hydrogen gas will normally contain minor amounts of one or more products of the hydrogenation reaction, i.e., 2,2,4,4-tetraalkylcyclobutane-1,3-diols, which have not been fully condensed in the product recovery stage downstream from the hydrogenation zone.

The catalyst of the present invention comprises ruthenium deposited on a carbon nanotube support. The term "support," as used in the context of the present specification and claims, is intended to have its commonly accepted meaning as would be well-understood by persons of ordinary skill in the art, that is, a nominally inert material on which a catalytically active material, e.g., typically a metal, is deposited on. The term, "deposited on," as used herein, is understood to mean any known method for adding the metal to the support including, but not limited to, depositing, adsorption, impregnation, ion-exchange, admixing, coprecipitation, and the like.

The catalyst comprises ruthenium supported on carbon nanotubes. Carbon nanotubes (also known as fibrils) are vermicular carbon deposits having diameters less than 1.0 μm, preferably less than 0.5 μm, and even more preferably less than 0.2 μm. Carbon nanotubes can be either multi-walled (i.e., have more than one graphene layer more or less parallel to the nanotube axis) or single walled (i.e., have only a single graphene layer parallel to the nanotube axis). Other types of carbon nanotubes are also known, such as fishbone fibrils (e.g., wherein the graphene sheets are disposed in a herringbone pattern with respect to the nanotube axis), etc. As produced, carbon nanotubes may be in the form of discrete nanotubes, aggregates of nanotubes (i.e., dense, microscopic particulate structure comprising entangled carbon nanotubes) or a mixture of both. Some representative examples of carbon nanotubes and their preparation are described in U.S. Patent Application Publication No.'s 2009 0208391; 2008 0176069; 2008 0175787; 2006 0239893; 2006 0142149; 2006 0142148; and 2003 0039604. Some forms of carbon nanotubes are available commercially from Hyperion Catalysis International, Inc.

The ruthenium may be loaded onto the nanotubes by any known method, such as ion exchange, impregnation, incipient wetness, precipitation, physical or chemical adsorption, or co-precipitation. Ruthenium may be provided as the zero valence metal or in oxidized form through compounds such as, for example, salts of inorganic or organic acids and organometallic complexes. In an exemplary embodiment, the ruthenium can be predeposited or loaded onto functionalized carbon nanotubes by ion exchange, i.e. mixing a solution containing ruthenium salts with the functionalized carbon nanotubes, allowing the salts to react with the functional groups of the functionalized nanotubes, and evaporating the remaining solution (e.g., the excess solvent from the solution). Alternatively, the ruthenium can be predeposited or loaded onto the carbon nanotubes by impregnation, or incipient wetness, i.e. wetting a mass of carbon nanotubes with a solution of metal salts and evaporating the solvent. Alternatively, metal salts may be caused to precipitate from solution in the presence of a mass of carbon nanotubes, causing the precipitated metal salts to physically or chemically adsorb on the nanotubes, followed by evaporation of the solvent. The ruthenium-loaded carbon nanotubes can be dried and the ruthenium reduced to ruthenium metal, if desired.

The carbon nanotube support may be further compounded with one or more binders to aid in pellet formation. The catalyst support along with any binder can be in any of the commonly used forms well-known in the art such as, for example, extrudates, chips, granules, monoliths, pellets, and the like for use in fixed-bed reactor processes or in powder form for slurry processes. The shape of the supports may include, but are not limited to, cylindrical, spheres, stars, monoliths, or any type of multiple-lobe shape. Depending on the particular support material employed and/or the method used to prepare a catalyst, the ruthenium may be deposited primarily on the surface of the support or distributed substantially throughout the support.

The catalyst can have a wide range of ruthenium content. Typically, the total amount of ruthenium present may be about 0.1 to about 10 weight percent based on the total weight of the catalyst. Some additional examples of ruthenium content are about 0.1 to about 9 weight percent, and about 0.2 to about 7 weight percent. For example, the catalyst can comprise about 1 to about 9 weight percent ruthenium deposited on a support comprising discrete carbon nanotubes, aggregates of carbon nanotubes, or a mixture thereof.

The temperature and hydrogen pressure also can be varied over a wide range depending on the activity of the catalyst, the mode of operation, selectivity considerations, and the desired rate of conversion. Typically, the process can be carried out under elevated hydrogen pressures of about 0.7 to about 42 MPa and at temperatures of about 75° C. to about 250° C. Some additional, ranges of hydrogen pressure are about 1.4 to about 21 MPa and about 2 to about 15 MPa. Some additional temperature ranges for the isomerization reaction about 100 to about 200° C. and about 100 to about 175° C. In one embodiment of the invention, for example, the 2,2,4,4-tetraalkylcyclobutane-1,3-dione can be contacted with hydrogen at a temperature of about 100 to about 200° C. and a pressure of about 1.4 to about 20.7 megapascals.

The 2,2,4,4-tetraalkylcyclobutane-1,3-diol hydrogenation product can have a range of cis to trans isomers 0:1 to about 2:1. For example, the hydrogenation of 2,2,4,4-tetramethylcyclobutane-1,3-dione can produce 2,2,4,4-tetramethylcyclobutane-1,3-diol having a cis:trans isomer ratio of about 0:8 to about 2:1. Some other representative examples of ranges of cis:trans ratios of the product 2,2,4,4-tetramethylcyclobutane-1,3-diol are 0.2:1 to about 1.8:1, about 0.5:1 to about 1.7:1, about 0.7:1 to about 1.6:1, and about 1:1 to about 1.5:1.

The process of the invention may be carried out in the absence or presence of a solvent. The solvent may be selected from a wide variety of compounds or mixture of compounds provided that they are liquid at the pressure at which the process is being operated, do not affect adversely the hydrogenation process, and are substantially inert or show limited reactivity (e.g., typically less than 1% conversion under process conditions) with respect to the catalyst, hydrogen, the tetraalkylcyclobutanedione starting material, and tetraalkylcyclobutanediol product. The starting 2,2,4,4-tetraalkylcyclobutane-1,3-dione, for example, can be dissolved in at least one solvent selected from water, alcohols, ethers, glycols, glycol ethers, alkanes, and esters. Some specific examples of solvents that may used in the isomerization process include, but are not limited to, water, methanol, ethanol, propanol, 1-butanol, 2-butanol, 2-ethylhexanol, 2,2-dimethyl-1,3-propanediol, ethylene glycol, propylene glycol, 1,4-butanediol, diethylene glycol, 2,2,4,4-tetramethylcyclobutane-1,3-diol, hexane, heptane, cyclohexane, octane, decane, diethyl ether, diisopropyl ether, tetrahydrofuran, methyl tert-butyl ether, ethylene glycol monobutyl ether, diethylene glycol monobutyl ether, ethyl acetate, n-propyl acetate, isopropyl isobutyrate, isobutyl propionate, octyl acetate, isobutyl isobutyrate, isobutyl acetate, methyl butyrate, and mixtures thereof. In one embodiment, for example, the solvent comprises isobutyl isobutyrate. Typically, the 2,2,4,4-tetraalkylcyclobutane-1,3-dione can be dissolved in the solvent at a concentration of about 1 to about 60 weight percent, based on the total weight of the tetraalkylcyclobutanedione solution. Some other examples of tetraalkylcyclobutanedione concentrations are about 5 to about 50 weight percent, and about 10 to about 25 weight percent. In another example, the tetraalkylcyclobutanedione comprises 2,2,4,4-tetramethylcyclobutanedione and is dissolved in a solvent comprising isobutyl isobutyrate at a concentration of about 1 to about 60 weight percent, about 5 to about 50 weight percent, or about 10 to about 25 weight percent. In another example, the hydrogenation is conducted in the absence of solvent by feeding the neat tetraalkylcyclobutanedione either alone or as a mixture in the tetraalkylcyclobutanediol hydrogenation product and/or hydrogenation byproducts to the hydrogenation process. For example, neat, molten 2,2,4,4-tetramethylcyclobutane-1,3-dione can be used alone or as a mixture with 2,2,4,4-tetramethylcyclobutane-1,3-diol and other hydrogenation products, including 1-hydroxy-2,2,4-trimethyl-3-pentanone, 3-hydroxy-2,2,4,4,-tetramethylcyclobutane-1-one, and 2,2,4-trimethyl-1,3-pentanediol, as the feed to the process.

The hydrogenation process can be carried out as a batch, semi-continuous or continuous process, and may utilize a variety of reactor types. Examples of suitable reactor types include, but are not limited to, stirred tank, continuous stirred tank, slurry, tubular, fixed bed, and trickle bed. The term "continuous" as used herein means a process wherein reactants are introduced and products withdrawn simultaneously in an uninterrupted manner. By "continuous" it is meant that the process is substantially or completely continuous in operation in contrast to a "batch" process. The term "batch" process as used herein means a process wherein all the reactants are added to the reactor and then processed according to a predetermined course of reaction during which no material is fed or removed into the reactor. For example, in a batch operation, a slurry of the catalyst in the tetraalkylcyclobutanedione and/or a solvent in which the tetraalkylcyclobutanedione has been dissolved is fed to a pressure vessel equipped with means for agitation. The pressure vessel is then pressurized with hydrogen to a predetermined pressure followed by heating to bring the reaction mixture to the desired temperature. After the reaction is complete the reaction mixture is removed from the pressure vessel, the catalyst is separated by filtration and the tetraalkylcyclobutanediol is isolated, for example, in a distillation train or by crystallization. The term "semicontinuous" means a process where some of the reactants are charged at the beginning of the process and the remaining reactants are fed continuously as the reaction progresses. Alternatively, a semicontinuous process may also include a process similar to a batch process in which all the reactants are added at the beginning of the process except that one or more of the products are removed continuously as the reaction progresses.

For economic and operability reasons, the process is advantageously operated as a continuous process. Continuous operation may utilize a fixed bed with a larger particle size of catalyst such as, for example, granules, pellets, various multilobal shaped pellets, rings, or saddles that are well known to skilled persons in the art. As an example of a continuous process, the catalyst bed may be fixed in a high pressure, tubular or columnar reactor and the liquid tetraalkylcyclobutanedione, dissolved in a solvent if desired, is fed continuously into the top of the bed at elevated pressure and temperature, and the crude hydrogenation product removed from the base of the reactor. Alternatively, it is possible to feed the tetraalkylcyclobutanedione into the bottom of the bed and remove the hydrogenated product from the top of the reactor. It is also possible to use 2 or more catalyst beds connected in parallel or in series to improve conversion, to reduce the quantity of catalyst, or to by pass a catalyst bed for periodic maintenance or catalyst removal. Another mode of continuous operation utilizes a slurry of the catalyst in an agitated pressure vessel which is equipped with a filter leg to permit continuous removal of a solution of the hydrogenated product in the tetraalkylcyclobutanedione and/or a solvent. In this manner a liquid reactant or reactant solution can be continuously fed to and a product solution continuously removed from an agitated pressure vessel containing an agitated slurry of the catalyst.

The process may be conducted in the liquid phase, the vapor phase, or as a combination of liquid and vapor phases. For example, the process may be carried in the vapor phase in a similar manner to the hydrogenation process disclosed in U.S. Pat. No. 5,395,987. In one example of a vapor phase operation, the process of the invention may be operated using vaporous feed conditions by feeding the tetraalkylcyclobutanedione in essentially liquid free, vaporous form to a hydrogenation zone comprising the supported ruthenium catalyst of the invention. Hence, the feed stream is introduced into the hydrogenation zone at a temperature which is above the dew point of the mixture. The term "dew point", as used herein, it well understood by persons skilled in the art and means that temperature at which a gas or a mixture of gases is saturated with respect to a condensable component. Typically, the feed temperature of the vaporous feed mixture to the hydrogenation zone is from about 5° C. to about 10° C. or more above its dew point at the operating pressure.

A convenient method of forming a vaporous mixture for use in a vapor phase process is to spray liquid tetraalkylcyclobutanedione or a tetraalkylcyclobutanedione solution into a stream of hot hydrogen-containing gas to form a saturated or partially saturated vaporous mixture. Alternatively, such a vapor mixture can be obtained by bubbling a hot hydrogen-containing gas through a body of the liquid tetraalkylcyclobutanedione or tetraalkylcyclobutanedione solution. If a saturated vapor mixture is formed it should then be heated further or diluted with more hot gas so as to produce a partially saturated vaporous mixture prior to contact with the catalyst. To maintain the vaporous feed stream above its dew point at the inlet end of a catalyst bed at the operating pressure, the hydrogen-containing gas: tetraalkylcyclobutanedione molar ratio is desirably about 10:1 to about 8000:1 or about 200:1 to about 1000:1.

Another embodiment of our invention is a process for the preparation of 2,2,4,4-tetramethylcyclobutane-1,3-diol, comprising continuously feeding 2,2,4,4-tetramethylcyclobutane-1,3-dione, a solvent, and hydrogen to a hydrogenation zone comprising a hydrogenation catalyst comprising about 2 to about 8 weight percent ruthenium, based on the total weight of the catalyst, deposited on a support comprising carbon nanotubes at a pressure of about 2 to about 15 megapascals and a temperature of about 120 to about 200° C. and continuously recovering from the hydrogenation zone an effluent comprising 2,2,4,4-tetramethylcyclobutane-1,3-diol. It will be apparent to persons skilled in the art that the various embodiments of cis:trans isomer ratios, catalyst support, reaction conditions of temperature and pressure, reactor formats, catalyst loadings, and solvents described hereinabove are encompassed also by the above process.

In one embodiment, for example, the process may further comprise continuously recycling a portion of the product effluent to the hydrogenation zone. As described previously, the hydrogenation zone may be any suitable reactor type including, but are not limited to, stirred tank, continuous stirred tank, slurry, tubular, fixed bed, and trickle bed. For example, the process of the invention may be carried out in a trickle bed reactor operated in the liquid phase.

The solvent can comprise an alcohol, ester, ether, 2,2,4,4-tetramethylcyclobutane-1,3-diol, water, or a mixture thereof. Some additional examples of solvents include water, methanol, ethanol, propanol, 1-butanol, 2-butanol, 2-ethylhexanol, 2,2-dimethyl-1,3-propanediol, ethylene glycol, propylene glycol, 1,4-butanediol, diethylene glycol, diethyl ether, diisopropyl ether, tetrahydrofuran, methyl tert-butyl ether, ethylene glycol monobutyl ether, diethylene glycol monobutyl ether, ethyl acetate, n-propyl acetate, isopropyl isobutyrate, isobutyl propionate, hexane, octane, pentane, isooctane, decane, cyclohexane, octyl acetate, isobutyl isobutyrate, methyl butyrate, isobutyl acetate, and mixtures thereof.

The cis:trans isomer ratio of the 2,2,4,4-tetramethylcyclobutane-1,3-diol hydrogenation product can be further modified by contacting the hydrogenation product with an isomerization catalyst. Our invention, therefore, further comprises contacting the 2,2,4,4-tetramethylcyclobutane-1,3-diol hydrogenation product, comprising cis and trans isomers, with hydrogen in the presence of an isomerization catalyst comprising ruthenium deposited on a support at a temperature of about 75 to about 250° C. to convert a portion of the trans isomer to the cis isomer.

The 2,2,4,4-tetramethylcyclobutane-1,3-diol hydrogenation product can have a cis:trans molar ratio of about 0.1:1 to about 2:1. Some other representative examples of ranges of cis:trans ratios of the 2,2,4,4-tetramethylcyclobutane-1,3-diol hydrogenation product are 0.2:1 to about 0.4:1, about 0.2:1 to about 0.7:1, about 0.2:1 to about 1:1, about 0.2:1 to about 1.2:1, about 0.5:1 to about 2:1, and about 0.8:1 to about 2:1.

The 2,2,4,4-tetramethylcyclobutane-1,3-diol hydrogenation product can be isomerized by contact with hydrogen in the presence of a supported ruthenium catalyst. The hydrogen can be fresh hydrogen or a mixture of fresh hydrogen and recycle hydrogen as described previously. The temperature and hydrogen pressure used in the isomerization step of the invention can also be varied over a wide range depending on the activity of the catalyst, the mode of operation, and the desired rate of conversion. Typically, the process can be carried out under elevated hydrogen pressures of up to about 50.66 MPa (megapascals) and at temperatures of about 75° C. to about 250° C. Some additional, more specific ranges of hydrogen pressures are about 0.3 to about 35 MPa, about 0.3 to about 5.2 MPa, about 0.3 to about 3.5 MPa, and about 0.4 to about 2.8 MPa. Some additional temperature ranges for the isomerization reaction about 100 to about 200° C. and about 100 to about 175° C. Persons of having ordinary skill in the art will recognize that any combination of the above temperatures and pressures can be used. In one embodiment of the invention, for example, the isomerization process can be carried at a temperature of about 100 to about 200° C. and a hydrogen pressure of about 0.4 to about 2.8 megapascals.

The isomerization catalyst comprises ruthenium deposited on a catalyst support. The support can be any recognized support material as described previously. For example, the support may comprise materials such as chromia, rare earth metal oxides, mixed metal oxides, zinc oxide, alumina, silica, silica-alumina, silicon carbide, zirconia, titania, activated carbon, graphite, graphitized carbon, carbon nanotubes, zeolites, or mixtures thereof and may include a binder to aid in pellet formation. The catalyst support along with any binder can be fabricated in any of the commonly used forms well-known in the art such as, for example, powders, extrudates, chips, granules, monoliths, pellets, cylinders, rings, saddles, spheres, stars, single lobe or multiple-lobe shapes, and the like.

In one embodiment, the isomerization catalyst comprises the same catalyst, e.g., ruthenium supported on carbon nanotubes, as described herein for the hydrogenation of 2,2,4,4-tetracyclobutane-1,3-dione. The total amount of ruthenium present in the isomerization catalyst can be about 0.1 to about 10 weight percent based on the total weight of the catalyst. Some additional examples of ruthenium content are about 0.1 to about 9 weight percent, and about 0.2 to about 7 weight percent. In one embodiment, for example, the isomerization catalyst will comprise about 0.1 to about 10 weight percent ruthenium, based on the total weight of the catalyst, deposited on a support comprising alumina, activated carbon, graphitized carbon, silica, silica-alumina, or carbon nanotubes.

The isomerization catalyst can be prepared by conventional techniques such as, for example, vapor deposition or impregnation of ruthenium compound into the support material. Ruthenium may be deposited on the support material using well-known methods as the metal itself or in the form of well-known ruthenium compounds such as, for example, ruthenium salts of inorganic or organic acids, ruthenium oxides, and organometallic complexes containing ruthenium. After the ruthenium compounds are deposited on the support material, the catalyst typically is dried and exposed to a reducing environment, e.g., hydrogen, in order to reduce the ruthenium compounds to ruthenium metal.

The isomerization step produces an isomerized 2,2,4,4-tetramethylcyclobutane-1,3-diol having a different ratio of cis to trans isomers than the starting 2,2,4,4-tetramethylcyclobutane-1,3-diol hydrogenation product and in which a portion of the trans isomer is converted to a cis isomer. For example, the starting 2,2,4,4-tetramethylcyclobutane-1,3-diol hydrogenation product can have a cis:trans isomer ratio of about 0:1 to about 1.1:1 and the isomerized 2,2,4,4-tetramethylcyclobutane-1,3-diol can have a cis:trans molar ratio of greater than 1:1 to about 2:1. In another example, the starting 2,2,4,4-tetramethylcyclobutane-1,3-diol hydrogenation product can have a cis:trans isomer ratio of about 0:1 to less than 1:1 and the isomerized 2,2,4,4-tetramethylcyclobutane-1,3-diol can have a cis:trans molar ratio of greater than 1:1 to about 1.2:1. In yet another example, the starting 2,2,4,4-tetramethylcyclobutane-1,3-diol hydrogenation product can have a cis:trans isomer ratio of about 0:1 to less than 1:1 and the isomerized 2,2,4,4-tetramethylcyclobutane-1,3-diol can have a cis:trans molar ratio of greater than 1:1 to about 1.5:1. In still another example, the 2,2,4,4-tetramethylcyclobutane- 1,3-diol hydrogenation product can have a cis:trans ratio of about 0.1:1 to about 1:1 and produces an isomerized 2,2,4,4-tetramethylcyclobutane-1,3-diol having a cis:trans ratio of about 0.4:1 to about 1.7:1.

The isomerization has no net production of 2,2,4,4-tetraalkylcyclobutane-1,3-diol. The phrase "net production" is intended to mean that no 2,2,4,4-tetra methyl-cyclobutane-1,3-diol in addition to that already present as the starting 2,2,4,4-tetramethylcyclobutane-1,3-diol hydrogenation product is generated over the course of the isomerization reaction. For example, 1 mole of a starting 2,2,4,4-tetramethylcyclobutane-1,3-diol hydrogenation product would be expected to produce about 1 mole or less (as a result of adventitious losses from handling, transfers, etc.) of isomerized 2,2,4,4-tetramethylcyclobutane-1,3-diol. Thus, the isomerization step of the instant invention would be distinguished from a hydrogenation process for the preparation of 2,2,4,4-tetramethylcyclobutane-1,3-diol from the corresponding dione because there would be a net increase in the amount of tetraalkylcyclobutanediol over the course of the hydrogenation process.

The isomerization step may be carried out using neat 2,2,4,4-tetramethylcyclobutane-1,3-diol or in the presence of a solvent that may be selected from a wide variety of compounds or mixture of compounds similar to those described for the hydrogenation of 2,2,4,4-tetramethylcyclobutane-1,3-dione. Some representative examples of solvents that may be used to dissolve the 2,2,4,4-tetramethylcyclobutane-1,3-diol include water, alcohols, ethers, glycols, glycol ethers, alkanes, esters, and mixtures thereof. Some specific examples of solvents that may used in the isomerization process include, but are not limited to, water, methanol, ethanol, propanol, 1-butanol, 2-butanol, 2-ethylhexanol, 2,2-dimethyl-1,3-propanediol, ethylene glycol, propylene glycol, 1,4-butanediol, diethylene glycol, hexane, heptane, cyclohexane, octane, decane, diethyl ether, diisopropyl ether, tetrahydrofuran, methyl tert-butyl ether, ethylene glycol monobutyl ether, diethylene glycol monobutyl ether, ethyl acetate, n-propyl acetate, isopropyl isobutyrate, isobutyl propionate, octyl acetate, isobutyl isobutyrate, isobutyl acetate, methyl butyrate, and mixtures thereof. In one embodiment, for example, the solvent comprises isobutyl isobutyrate. Typically, the 2,2,4,4-tetramethylcyclobutane-1,3-diol can be dissolved in the solvent at a concentration of about 1 to about 60 weight percent, based on the total weight of the tetraalkylcyclobutanediol solution. Some other examples of 2,2,4,4-tetramethylcyclobutane-1,3-diol concentrations are about 5 to about 50 weight percent, and about 10 to about 25 weight percent.

The hydrogenation process of the invention may be coupled with a process to prepare 2,2,4,4-tetramethylcyclobutane-1,3-dione from isobutyric anhydride to form an integrated process for the preparation of 2,2,4,4-tetramethylcyclobutane-1,3-diol. Yet another embodiment of our invention, therefore, is process for the preparation of 2,2,4,4-tetramethylcyclobutane-1,3-diol, comprising:

(1) feeding isobutyric anhydride to a pyrolysis zone produce a vapor effluent comprising dimethylketene, isobutyric acid and unreacted isobutyric anhydride;
(2) cooling the vapor effluent to condense isobutyric acid and isobutyric anhydride and separating the condensate from the dimethylketene vapor;
(3) feeding the dimethylketene vapor to an absorption zone wherein the dimethylketene vapor is contacted with and dissolved in a solvent to produce an effluent comprising a solution of dimethylketene in the solvent;
(4) feeding the absorption zone effluent to a dimerization zone wherein the effluent is heated to convert dimethylketene to 2,2,4,4-tetramethylcyclobutane-1,3-dione to produce an effluent comprising a solution of the 2,2,4,4-tetramethylcyclobutane-1,3-dione in the solvent; and
(5) contacting the effluent of 2,2,4,4-tetramethylcyclobutane-1,3-dione with hydrogen in the presence of a catalyst comprising ruthenium deposited on a catalyst support comprising carbon nanotubes to form a 2,2,4,4-tetramethylcyclobutane-1,3-diol.

The first step of the process involves feeding isobutyric anhydride, usually in combination with an inert gas such as nitrogen, to the pyrolysis zone wherein the isobutyric anhydride is heated at about 350 to 600° C. under reduced pressure, e.g., 20 to 500 torr. Typical conditions are temperatures in the range of 400 to 500° C. and pressures of 40 to 250 torr. The contact or residence time of the reactant and product within the pyrolysis zone typically is in the range of about 0.1 to 8 seconds, depending on the temperatures and pressures employed. Step (1), generally, is carried out to achieve an average butyric anhydride conversion of at least 30% and, typically, about 50 to 90%.

The second step of the process comprises rapidly cooling the pyrolysis effluent to condense the isobutyric acid by product of the pyrolysis reaction and unreacted butyric anhydride and separating the condensed liquids from the dimethylketene vapor to minimize the reaction of the isobutyric acid and dimethyl ketene. Cooling of the vapor stream may be accomplished using conventional equipment such as one or more heat exchangers or externally cooled cyclones which provide efficient heat removal. The cooling required by the second step normally should reduce the temperature of the pyrolysis effluent to at least 40° C. and, typically, about 20 to 30° C. The condensed isobutyric acid and isobutyric anhydride may be separated from the gaseous dimethylketene by conventional gas liquid separation means such as one or more cyclones. When the pyrolysis step is carried out under reduced pressure, the temperature reduction and separation of the second step normally are performed at pressures substantially the same as those existing within the pyrolysis zone.

In the third step of our novel process, the highly volatile dimethylketene vapor from the second step is drawn through vacuum pump(s) and fed to the absorption zone wherein it is contacted with and dissolved in an inert solvent comprising liquid (melted) 2,2,4,4 tetramethylcyclobutane 1,3-dione. The vacuum pump(s) used to reduce the pressure of the pyrolysis or cracking and the cooling separation zones, generally, is of a type which does not require a liquid seal. The absorption zone typically is operated at a temperature of about 10 to 150° C., for example, about 115 to 120° C., and a pressure of about 1 to 3 atmospheres absolute to keep the dione extractant in the liquid phase. Essentially all of the dimethylketene absorbed by the dione dimerizes to the dione. Increasing the pressure within the absorption zone generally will result in increased absorption of the dimethylketene.

The absorption zone comprises apparatus which provides for intimate contact between the dimethylketene vapor and the liquid solvent. For example, the apparatus may consist of one or more columns equipped with packing material or trays wherein the dimethylketene vapor is fed at or near the bottom of the column and the solvent is fed at or near the top of the column resulting in the dissolution of the ascending gas by the descending liquid solvent. The flow rate of the dione through the absorber preferably gives a 4% solution of dimethylketene.

The dimerization zone of the fourth step may comprise any apparatus which permits the step (3) effluent to be maintained at a temperature of about 120 to 140° C. for a period of time, e.g., a residence time of about 50 to 80 minutes, sufficient to convert substantially all of the dimethylketene in the effluent to 2,2,4,4-tetramethylcyclobutanedione. Thus, the dimerization zone may consist of an agitated vessel equipped with means to heat the step (3) effluent. The product effluent of the dimerization zone consists essentially of 2,2,4,4 tetramethylcyclobutanedione. A portion of the product dione equivalent to the amount of dimethylketene fed to the absorption zone is fed to the hydrogenation zone. The remaining dione is recirculated to the absorption zone.

The final step of our process comprises the hydrogenation of the 2,2,4,4 tetramethylcyclobutanedione present in the step (4) effluent contacting the effluent from step (4) with hydrogen in the presence of a catalyst comprising ruthenium deposited on a catalyst support comprising carbon nanotubes to form a 2,2,4,4-tetramethylcyclobutane-1,3-diol in accordance with the process conditions and other embodiments of the hydrogenation processes described herein for the conversion of 2,2,4,4-tetraalkylcyclobutane-1,3-diones to their corresponding diols. It is understood, therefore, that all aspects of the ruthenium carbon nanotube catalysts, hydrogenation conditions of temperature and pressure, solvents, etc., as described hereinabove are included by reference for the hydrogenation step of the above integrated process.

For example, the catalyst can comprise about 1 to about 9 weight percent ruthenium, the support can comprise discrete carbon nanotubes, aggregates of carbon nanotubes, or a mixture thereof; and the solvent can comprise an ester, ether, 2,2,4,4-tetramethylcyclobutane-1,3-diol, water, or a mixture thereof. The effluent from step (3) comprising 2,2,4,4-tetraalkylcyclobutane-1,3-dione can be contacted with hydrogen at a temperature of about 100 to about 200° C. and a pressure of about 1.4 to about 20.7 megapascals.

The solvent may be selected from water, alcohols, ethers, glycols, glycol ethers, alkanes, esters, and mixtures thereof. Some specific examples of solvents that may used in the hydrogenation process include, but are not limited to, water, methanol, ethanol, propanol, 1-butanol, 2-butanol, 2-ethylhexanol, 2,2-dimethyl-1,3-propanediol, ethylene glycol, propylene glycol, 1,4-butanediol, diethylene glycol, 2,2,4,4-tetramethylcyclobutane-1,3-diol, hexane, heptane, cyclohexane, octane, decane, diethyl ether, diisopropyl ether, tetrahydrofuran, methyl tert-butyl ether, ethylene glycol monobutyl ether, diethylene glycol monobutyl ether, ethyl acetate, n-propyl acetate, isopropyl isobutyrate, isobutyl propionate, octyl acetate, isobutyl isobutyrate, isobutyl acetate, methyl butyrate, and mixtures thereof. In one embodiment, for example, the solvent comprises isobutyl isobutyrate. The hydrogenation step can be carried out as a batch, semi-continuous or continuous process, and may utilize a variety of reactor types, including, but are not limited to, stirred tank, continuous stirred tank, slurry, tubular, fixed bed, and trickle bed.

Embodiment A is a process for the preparation of a 2,2,4,4-tetraalkylcyclobutane-1,3-diol, comprising contacting a 2,2,4,4-tetraalkylcyclobutane-1,3-dione having the formula (I):

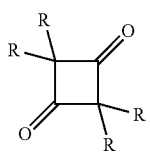

with hydrogen in the presence of a catalyst comprising about 0.1 to about 10 weight percent ruthenium, based on the total weight of the catalyst, deposited on a support comprising carbon nanotubes to form a 2,2,4,4-tetraalkylcyclobutane-1,3-diol having the formula (II):

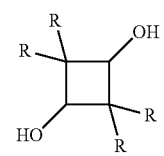

wherein R is a alkyl radical containing 1 to 8 carbon atoms.

The process of Embodiment A wherein R is methyl, ethyl, propyl, butyl, pentyl, hexyl, heptyl, or octyl.

The process of Embodiment A or Embodiment A with any of the intervening features wherein R is methyl.

The process of Embodiment A or Embodiment A with any of the intervening features wherein the catalyst comprises about 1 to about 9 weight percent ruthenium and the support comprises discrete carbon nanotubes, aggregates of carbon nanotubes, or a mixture thereof.

The process of Embodiment A or Embodiment A with any of the intervening features wherein the 2,2,4,4-tetraalkylcyclobutane-1,3-dione is contacted with the hydrogen at a temperature of about 100 to about 200° C. and a pressure of about 1.4 to about 20.7 megapascals.

The process of Embodiment A or Embodiment A with any of the intervening features wherein the 2,2,4,4-tetraalkylcyclobutane-1,3-dione is dissolved in at least one solvent selected from water, alcohols, ethers, glycols, glycol ethers, alkanes, esters and mixtures thereof.

The process of Embodiment A or Embodiment A with any of the intervening features wherein the solvent is selected from water, methanol, ethanol, propanol, 1-butanol, 2-butanol, 2-ethylhexanol, 2,2-dimethyl-1,3-propanediol, ethylene glycol, propylene glycol, 1,4-butanediol, 2,2,4,4-tetramethylcyclobutane-1,3-diol, cyclohexanol, diethylene glycol, hexane, heptane, cyclohexane, octane, decane, diethyl ether, diisopropyl ether, tetrahydrofuran, methyl tert-butyl ether, ethylene glycol monobutyl ether, diethylene glycol monobutyl ether, ethyl acetate, n-propyl acetate, isopropyl isobutyrate, isobutyl propionate, octyl acetate, isobutyl isobutyrate, isobutyl acetate methyl butyrate, and mixtures thereof.

The process of Embodiment A or Embodiment A with any of the intervening features wherein the 2,2,4,4-tetraalkylcyclobutane-1,3-diol comprises 2,2,4,4-tetramethylcyclobutane-1,3-diol having a cis:trans molar ratio of about 0.8:1 to about 2:1.

The process of Embodiment A or Embodiment A with any of the intervening features wherein the process is a continuous process.

The process of Embodiment A or Embodiment A with any of the intervening features wherein the process is conducted in the liquid phase, vapor phase, or a combination of liquid and vapor phase.

Embodiment B is the process of Embodiment A or Embodiment A with any of the intervening features wherein the 2,2,4,4-tetraalkylcyclobutane-1,3-dione is 2,2,4,4-tetramethylcyclobutane-1,3-dione, and the process comprises continuously feeding 2,2,4,4-tetramethylcyclobutane-1,3-dione, a solvent, and hydrogen to a hydrogenation zone comprising a hydrogenation catalyst comprising about 2 to about 8 weight percent ruthenium, based on the total weight of the catalyst, deposited on a support comprising carbon nanotubes at a pressure of about 2 to about 15 megapascals and a temperature of about 120 to about 200° C. and continuously recovering from the hydrogenation zone an effluent comprising 2,2,4,4-tetramethylcyclobutane-1,3-diol.

The process of Embodiment B further comprising continuously recycling a portion of the effluent to the hydrogenation zone.

The process of Embodiment B or Embodiment B with any of the intervening features wherein the solvent comprises an alcohol, ester, ether, 2,2,4,4-tetramethylcyclobutane-1,3-diol, water, or a mixture thereof.

The process of Embodiment B or Embodiment B with any of the intervening features wherein the 2,2,4,4-tetramethylcyclobutane-1,3-diol comprises cis and trans isomers and further comprising contacting the 2,2,4,4-tetramethylcyclobutane-1,3-diol with hydrogen in the presence of an isomerization catalyst comprising ruthenium deposited on a support at a temperature of about 75 to about 250° C. to convert a portion of the trans isomer to the cis isomer.

The process of Embodiment B or Embodiment B with any of the intervening features wherein the isomerization catalyst comprises about 0.1 to about 10 weight percent ruthenium, based on the total weight of the isomerization catalyst, and the support comprises alumina, carbon, silica, silica-alumina, activated carbon, graphitized carbon, or carbon nanotubes.

A process that includes Embodiment A, Embodiment A with any of the intervening features, Embodiment B, or Embodiment B with any of the intervening features wherein the 2,2,4,4-tetraalkylcyclobutane-1,3-dione is 2,2,4,4-tetramethyl-cyclobutane-1,3-dione and is prepared by:
(1) feeding isobutyric anhydride to a pyrolysis zone produce a vapor effluent comprising dimethylketene, isobutyric acid and unreacted isobutyric anhydride;
(2) cooling the vapor effluent to condense isobutyric acid and isobutyric anhydride and separating the condensate from the dimethylketene vapor;
(3) feeding the dimethylketene vapor to an absorption zone wherein the dimethylketene vapor is contacted with and dissolved in a solvent to produce an effluent comprising a solution of dimethylketene in the solvent;
(4) feeding the absorption zone effluent to a dimerization zone wherein the effluent is heated to convert dimethylketene to 2,2,4,4-tetramethylcyclobutane-1,3-dione to produce an effluent comprising a solution of the 2,2,4,4-tetramethylcyclobutane-1,3-dione in the solvent;

The process of the invention are further described and illustrated by the following examples.

EXAMPLES

All percentages are by weight and all pressures are reported as gauge unless specified otherwise. The carbon nanotube support material used in the examples was 1.6 mm (1/16 inch) extrudates obtained from Hyperion Catalyst International, Inc. Catalyst surface areas were measured volumetrically using the Brunauer-Emmett-Teller (BET) method. Analysis of reaction products was performed by gas chromatography using a DB™-Wax column (30 meters×0.25 mm ID, 0.5 micron film thickness) over a temperature range of 50 to 240° C. and a flame ionization detector. The reaction samples were dissolved in dimethyl sulfoxide before injection into the gas chromatograph. Throughout the examples, the percent conversion of 2,2,4,4-tetramethylcyclobutane-1,3-dione (abbreviated herein as "dione") is defined as:

$$\frac{\text{Moles dione converted to products}}{\text{Moles dione fed to the reactor}} \times 100$$

The percent selectivity to 2,2,4,4-tetramethylcyclobutane-1,3-diol (abbreviated herein as "diol") is defined as:

$$\frac{\text{Moles dione converted to diol}}{\text{Moles dione converted to all products}} \times 100$$

Typical by-products of the hydrogenation reaction were 2,2,4-trimethyl-1,3-pentanediol, 2,4-dimethyl-3-pentanol (diisopropyl carbinol), 2,2,4-trimethyl-3-pentanol, 2,2,4-trimethyl-1-pentanol, and 2,2,4-trimethyl-3-oxo-1-pentanol. Trace amounts of methane also were produced from the hydrogenation of the isobutyl butyrate solvent. All pressures are reported as gauge unless indicated otherwise.

Preparation of Ru/carbon nanotube catalysts—This example illustrates a procedure for the preparation of a ruthenium and carbon nanotube catalyst by using a wet impregnation method. Carbon nanotube extrudates (20 g, 1/16", surface area=244 m²/g) were charged to a 100 mL glass bottle, cooled in a dry ice bath, followed by 44 g of a 2% ruthenium acetoacetate solution in acetone added dropwise. The impregnated carbon nanotube extrudates were dried at ambient temperature for 4 hours and then in an oven at 120° C. for 2 hours. Then, the dried extrudates were then loaded in a ½" stainless steel tube and exposed to 200 standard cubic centimeters per minute (SCCM) of 10% hydrogen in nitrogen at 180° C. for 2 hours. The nominal Ru loading was 1 wt %.

Comparative Example 1

A mixture of 18 g of dione, 160 g of isobutyl isobutyrate (IBIB), and 15 g of a catalyst containing 2 weight percent Ru on an α-alumina support and having a surface area of 40 m²/g (obtained from BASF Catalysts), was charged to a 300 mL stainless steel autoclave. The catalyst was placed in a stainless steel catalyst basket within the autoclave. The autoclave was agitated and purged twice with nitrogen (0.069 MPa, 10 psig) at an ambient temperature and then purged with hydrogen (0.069 MPa, 10 psig). The autoclave was then heated to 130° C. and pressurized with hydrogen (2.76 MPa, 400 psig). After 2 hours, a product sample was taken and analyzed by gas chromatography (GC). The conversion of dione was 94% and the selectivity to diol was 41%. The cis:trans isomer ratio of the diol was 1.02.

Comparative Example 2

A pre-reduced catalyst (2.5 g) containing 7 weight percent Ru on a graphitized carbon support (purchased from BASF Catalysts under the designation "C3610") and having a surface area of 589 m²/g was loaded in a 300 mL stainless steel autoclave in a stainless steel catalyst basket with 18 g of dione and 160 g of IBIB. The autoclave was agitated and purged twice with nitrogen (0.069 MPa, 10 psig) at an ambient temperature and then purged with hydrogen (0.069 MPa, 10 psig). The autoclave was then heated to 130° C. and pressurized with hydrogen (2.76 MPa, 400 psig). After 1 hour, a product sample was taken and analyzed by GC. The conversion of dione was 55% and the selectivity to diol was 29%. The cis:trans isomer ratio of the diol was 1.06.

Comparative Example 3

A 2 wt % Ru on silica catalyst (2.5 g, surface area=300 m²/g, obtained from BASF Catalysts) was charged to a 300 mL stainless steel autoclave in a stainless steel catalyst basket, followed by 18 g of dione and 160 g of IBIB. The autoclave was agitated, purged twice with nitrogen (0.069 MPa, 10 psig) at ambient temperature, and purged with hydrogen (0.069 MPa, 10 psig). The autoclave was then heated to 130° C. and pressurized with hydrogen (2.76 MPa, 400 psig). After 1 hour, a product sample was taken and analyzed by GC. The conversion of dione was 52% and the selectivity to diol was 30%. The cis:trans isomer ratio of the diol was 1.06.

Example 1

A 3 wt % Ru on carbon nanotube catalyst (0.5 g, surface area=244 m²/g) was loaded in a 100 mL stainless steel autoclave in a stainless steel catalyst basket with 6 g of dione and 54 g of IBIB. The autoclave was agitated, purged twice with helium (0.69 MPa, 100 psig) at ambient temperature, and purged with hydrogen (0.69 MPa, 100 psig). The autoclave was then heated to 130° C. and pressurized with hydrogen (2.76 MPa, 400 psig). After 1 hour, a product sample was taken and analyzed by GC. The conversion of dione was 99.9% and the selectivity to diol was 91%. The cis:trans isomer ratio of the diol was 1.04.

Example 2

A 3 wt % Ru on carbon nanotube catalyst (0.5 g, surface area=244 m²/g) was loaded in a 100 mL stainless steel autoclave in a stainless steel catalyst basket with 6 g of dione and 54 g of IBIB. The autoclave was agitated, purged twice with helium (0.69 MPa, 100 psig) at ambient temperature, and purged with hydrogen (0.69 MPa, 100 psig). The autoclave was then heated to 140° C. and pressurized with hydrogen (2.76 MPa, 400 psig). After 1 hour, a product sample was taken and analyzed by GC. The conversion of dione was 100% and the selectivity to diol was 87%. The cis:trans isomer ratio of the diol was 1.08.

Example 3

A 3 wt % Ru on carbon nanotube catalyst (0.5 g, surface area=244 m²/g) was loaded in a 100 mL stainless steel autoclave in a stainless steel catalyst basket with 6 g of dione and 54 g of IBIB. The autoclave was agitated, purged twice with helium (0.69 MPa, 100 psig) at ambient temperature, and purged with hydrogen (0.69 MPa, 100 psig). The autoclave was then heated to 120° C. and pressurized with hydrogen (2.76 MPa, 400 psig). After 1 hour, a product sample was taken and analyzed by GC. The conversion of dione was 99.9% and selectivity to diol was 94%. The cis:trans isomer ratio of the diol was 1.07.

Comparative Example 4

This example followed a similar procedure to Example 1 of U.S. Pat. No. 2,936,324 using 5 weight percent Ru on carbon catalyst, except that a higher temperature and lower pressure were used. A 5 wt % Ru on activated carbon powder catalyst (obtained from Engelhard, now BASF Catalysts, surface area=881 m²/g) was dried in a conventional oven at 105° C. overnight. The dried catalyst (1.33 g) was loaded in a 100 mL stainless steel autoclave reactor. The autoclave was purged twice with helium (0.69 MPa, 100 psig) and then with hydrogen at ambient temperature. After the autoclave was heated to 150° C., the reactor pressure was increased to 2.76 MPa (400 psig) with hydrogen. After 1 hour, the reactor was cooled to about 50° C. and 26.7 g of dione and 66.7 g of methanol were added. The autoclave was agitated and purged twice with helium (0.69 MPa, 100 psig) and then with hydrogen (0.69 MPa, 100 psig). The autoclave was then heated to 140° C. and pressurized to 2.76 MPa (400 psig). After 1 hour, a product sample was taken and analyzed by GC. The conversion of dione was 99.7% and the selectivity to diol was 85.8%. The cis:trans isomer ratio of the diol was 0.84.

Comparative Example 5

Ru powder (0.1 g, purchased from Aldrich Chemical Co.) was loaded in a 100 mL stainless steel autoclave reactor with 64 g of IBIB. The autoclave was agitated, purged twice with helium (0.69 MPa, 100 psig), and purged with hydrogen at ambient temperature. The autoclave was heated to 150° C. and the reactor pressure was increased to (2.76 MPa, 400 psig) with hydrogen. After 1 hour, the reactor was cooled to approximately 50° C., and 6 g of dione were added. The autoclave was agitated and purged twice with helium (0.69 MPa, 100 psig) followed by hydrogen. The autoclave was then heated to 140° C. and pressurized with hydrogen to 2.76 MPa (400 psig). After 1 hour, a product sample was taken and analyzed by GC. The conversion of dione was 99.8% and the yield of diol was 59.5%. The cis:trans isomer ratio of the diol was 1.11.

The invention claimed is:

1. A process for the preparation of a 2,2,4,4-tetraalkylcyclobutane-1,3-diol, comprising contacting a 2,2,4,4-tetraalkylcyclobutane-1,3-dione having the formula (I):

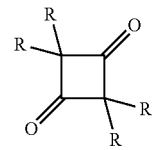

with hydrogen in the presence of a catalyst comprising about 0.1 to about 10 weight percent ruthenium, based on the total weight of the catalyst, deposited on a support comprising carbon nanotubes to form a 2,2,4,4-tetraalkylcyclobutane-1,3-diol having the formula (II):

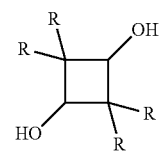

wherein R is a alkyl radical containing 1 to 8 carbon atoms.

2. The process according to claim 1 wherein R is methyl, ethyl, propyl, isopropyl, butyl, isobutyl, pentyl, isoamyl, hexyl, heptyl, or octyl.

3. The process according to claim 2 wherein R is methyl.

4. The process according to claim 3 wherein the catalyst comprises about 1 to about 9 weight percent ruthenium and the support comprises discrete carbon nanotubes, aggregates of carbon nanotubes, or a mixture thereof.

5. The process according to claim 4 wherein the 2,2,4,4-tetraalkylcyclobutane-1,3-dione is contacted with the hydrogen at a temperature of about 100 to about 200° C. and a pressure of about 1.4 to about 20.7 megapascals.

6. The process according to claim 5 wherein the 2,2,4,4-tetraalkylcyclobutane-1,3-dione is dissolved in at least one solvent selected from the group consisting of water, alcohols, ethers, glycols, glycol ethers, alkanes, esters, and mixtures thereof.

7. The process according to claim 6 wherein the solvent is selected from the group consisting of water, methanol, ethanol, propanol, 1-butanol, 2-butanol, 2-ethylhexanol, 2,2-dimethyl-1,3-propanediol, ethylene glycol, propylene glycol, 1,4-butanediol, 2,2,4,4-tetramethylcyclobutane-1,3-diol, cyclohexanol, diethylene glycol, hexane, heptane, cyclohexane, octane, decane, diethyl ether, diisopropyl ether, tetrahydrofuran, methyl tert-butyl ether, ethylene glycol monobutyl ether, diethylene glycol monobutyl ether, ethyl acetate, n-propyl acetate, isopropyl isobutyrate, isobutyl propionate, octyl acetate, isobutyl isobutyrate, isobutyl acetate, methyl butyrate, and mixtures thereof.

8. The process according to claim 1 wherein the 2,2,4,4-tetraalkylcyclobutane-1,3-diol comprises 2,2,4,4-tetramethylcyclobutane-1,3-diol having a cis:trans molar ratio of about 0.8:1 to about 2:1.

9. The process according to claim 1 wherein the process is a continuous process.

10. A process for the preparation of 2,2,4,4-tetramethylcyclobutane-1,3-diol, comprising continuously feeding 2,2,4,4-tetramethylcyclobutane-1,3-dione, a solvent, and hydrogen to a hydrogenation zone comprising a hydrogenation catalyst comprising about 2 to about 8 weight percent ruthenium, based on the total weight of the catalyst, deposited on a support comprising carbon nanotubes at a pressure of about 2 to about 15 megapascals and a temperature of about 120 to about 200° C. and continuously recovering from the hydrogenation zone an effluent comprising 2,2,4,4-tetramethylcyclobutane-1,3-diol.

11. The process according to claim 10 further comprising continuously recycling a portion of the effluent to the hydrogenation zone.

12. The process according to claim 10 wherein the solvent comprises an alcohol, ester, ether, 2,2,4,4-tetramethylcyclobutane-1,3-diol, water, or a mixture thereof.

13. The process according to claim 10 wherein the 2,2,4,4-tetramethylcyclobutane-1,3-diol comprises cis and trans isomers and the process further comprises contacting the 2,2,4,4-tetramethylcyclobutane-1,3-diol with hydrogen in the presence of an isomerization catalyst comprising ruthenium deposited on a support at a temperature of about 75 to about 250° C. to convert a portion of the trans isomer to the cis isomer.

14. The process according to claim 13 wherein the isomerization catalyst comprises about 0.1 to about 10 weight percent ruthenium, based on the total weight of the isomerization catalyst, and the support comprises alumina, carbon, silica, silica-alumina, activated carbon, graphitized carbon, or carbon nanotubes.

15. A process for the preparation of 2,2,4,4-tetramethylcyclobutane-1,3-diol, comprising
(1) feeding isobutyric anhydride to a pyrolysis zone to produce a vapor effluent comprising dimethylketene, isobutyric acid and unreacted isobutyric anhydride;
(2) cooling the vapor effluent to condense isobutyric acid and isobutyric anhydride and separating the condensate from the dimethylketene vapor;
(3) feeding the dimethylketene vapor to an absorption zone wherein the dimethylketene vapor is contacted with and dissolved in a solvent to produce an effluent comprising a solution of dimethylketene in the solvent;
(4) feeding the absorption zone effluent to a dimerization zone wherein the effluent is heated to convert dimethylketene to 2,2,4,4-tetramethylcyclobutane-1,3-dione to produce an effluent comprising a solution of the 2,2,4,4-tetramethylcyclobutane-1,3-dione in the solvent; and
(5) contacting the 2,2,4,4-tetramethylcyclobutane-1,3-dione with hydrogen in the presence of a catalyst comprising ruthenium deposited on a catalyst support comprising carbon nanotubes to form a 2,2,4,4-tetramethylcyclobutane-1,3-diol.

16. The process according to claim 15 wherein the catalyst comprises about 1 to about 9 weight percent ruthenium, the support comprises discrete carbon nanotubes, aggregates of carbon nanotubes, or a mixture thereof; the solvent comprises an ester, ether, 2,2,4,4-tetramethylcyclobutane-1,3-diol, water, or a mixture thereof; and the 2,2,4,4-tetraalkylcyclobutane-1,3-dione is contacted with the hydrogen at a temperature of about 100 to about 200° C. and a pressure of about 1.4 to about 20.7 megapascals.

* * * * *